(12) United States Patent
Lai

(10) Patent No.: US 10,792,101 B2
(45) Date of Patent: Oct. 6, 2020

(54) MELANIN ABLATION GUIDED BY STEPWISE MULTI-PHOTON ACTIVATED FLUORESCENCE

(71) Applicant: Zhenhua Lai, Fremont, CA (US)

(72) Inventor: Zhenhua Lai, Fremont, CA (US)

(73) Assignee: Zhenhua Lai, Fremont, CA (US)

(*) Notice: Subject to any disclaimer, the term of this patent is extended or adjusted under 35 U.S.C. 154(b) by 0 days.

(21) Appl. No.: 16/717,330

(22) Filed: Dec. 17, 2019

(65) Prior Publication Data

US 2020/0197091 A1 Jun. 25, 2020

Related U.S. Application Data

(62) Division of application No. 15/323,475, filed as application No. PCT/US2015/038941 on Jul. 2, 2015, now Pat. No. 10,507,059.

(60) Provisional application No. 62/020,459, filed on Jul. 3, 2014.

(51) Int. Cl.
*A61B 18/20* (2006.01)
*A61B 18/00* (2006.01)
*A61B 5/00* (2006.01)

(52) U.S. Cl.
CPC ........ *A61B 18/203* (2013.01); *A61B 5/0071* (2013.01); *A61B 2018/00452* (2013.01); *A61B 2018/00476* (2013.01); *A61B 2018/00577* (2013.01); *A61B 2018/00785* (2013.01); *A61B 2018/20359* (2017.05)

(58) Field of Classification Search
CPC ........ A61B 18/203; A61B 2018/20359; A61B 5/0071; A61B 2018/00452; A61B 2018/00476; A61B 2018/00577; A61B 2018/00785
USPC .......................................................... 606/9
See application file for complete search history.

(56) References Cited

U.S. PATENT DOCUMENTS

| | | | |
|---|---|---|---|
| 10,507,059 B2* | 12/2019 | Lai | A61B 18/203 |
| 2005/0186565 A1* | 8/2005 | Malak | G01N 21/648 |
| | | | 435/5 |
| 2005/0203495 A1* | 9/2005 | Malak | A61K 8/72 |
| | | | 606/9 |
| 2012/0059307 A1* | 3/2012 | Harris | A61P 21/00 |
| | | | 604/20 |

* cited by examiner

*Primary Examiner* — Aaron F Roane
(74) *Attorney, Agent, or Firm* — Verrill Dana, LLP

(57) ABSTRACT

A method and system of ablating melanin are provided. Stepwise multi-photon fluorescence is induced in melanin within a region of tissue. The fluorescence is detected, and at least a portion of the melanin from which the fluorescence is detected is ablated. The system and method can use a continuous wave laser in the near infrared range for the inducement and ablation of melanin, providing high resolution at low cost.

22 Claims, 18 Drawing Sheets

MELANIN ABLATION GUIDED BY STEPWISE MULTI-PHOTON ACTIVATED FLUORESCENCE

CROSS REFERENCE TO RELATED APPLICATIONS

This application claims priority of U.S. Provisional Application No. 62/020,459 filed 3 Jul. 2014, and to PCT Application No. PCT/US2015/038941, filed 2 Jul. 2015, and is a divisional application of U.S. application Ser. No. 15/323,475, filed 3 Jan. 2017. Each of the aforementioned applications is hereby incorporated by reference in its entirety.

STATEMENT REGARDING FEDERALLY SPONSORED RESEARCH OR DEVELOPMENT

N/A

BACKGROUND

Melanin, a ubiquitous biological pigment produced by melanocytes in most organisms, is an important component of animal pigmentary systems. Naturally occurring pigmentation that determines hair, eye and skin coloration is attributed to two types of melanin: eumelanin and pheomelanin. Eumelanin is the dominant component of brown and black pigments in dark skin and black hair, while pheomelanin is more common in yellow and red pigments in hair. Melanin has not been well understood, as it is an insoluble polymer without a well-defined structure, which makes it difficult to isolate and study.

Melanin is related to many skin diseases, such as malignant melanoma, the most aggressive skin cancer; vitiligo, a disease characterized by the loss of melanin pigment; melasma, an acquired brown hypermelanosis of the face; solar lentigines and ephelides, benign pigmented spots that are associated with an increased risk of skin cancer; and nevus of Ota, a syndrome comprising a grayish-blue, macular discoloration affecting the sclera of an eye and the ipsilateral facial skin in the area of the distribution of the corresponding trigeminal nerve.

Selective photothermolysis has been widely used for treatments of melanin-related skin diseases. This technique utilizes nanosecond-domain laser pulses to selectively ablate melanin and melanin-related cells. Despite its effectiveness, photothermolysis lacks the ability to target individual melanin particles, which limits its usage in treating skin diseases in some sensitive regions, such as nevus of Ota around the eye.

SUMMARY OF THE INVENTION

The invention relates to a method and system for ablation of melanin guided by the stepwise multi-photon activation of melanin in a region of tissue. A method of ablating melanin includes the steps of inducing the stepwise multi-photon fluorescence in melanin within the region of tissue, detecting the fluorescence from the melanin, and ablating at least a portion of the melanin from which the fluorescence is detected.

The method and system can achieve high resolutions to ablate melanin with no or minimal collateral damage to surrounding tissue. The method and system are useful for treating a variety of melanin-related diseases and conditions in human and non-human subjects.

Other aspects of the method and system include the following:

1. A method of ablating melanin comprising:
   inducing stepwise multi-photon fluorescence in melanin within a region of tissue;
   detecting the fluorescence from the melanin in the region; and
   ablating at least a portion of the melanin from which the fluorescence is detected.
2. The method of item 1, wherein the step of inducing fluorescence in the melanin comprises transmitting a beam of laser light from a continuous wave laser source to the region of tissue to activate fluorescence from the melanin within the region.
3. The method of item 2, wherein a wavelength of the laser light ranges from 600 nm to 2 μm.
4. The method of any of the preceding items, wherein the beam of laser light is scanned across an image plane.
5. The method of any of the preceding items, wherein the beam of laser light is scanned across multiple image planes, each image plane located at a different depth within the region of tissue.
6. The method of any of the preceding items, wherein the beam of laser light penetrates the region of tissue to a depth between a surface and 500 μm.
7. The method of any of items 1-5, wherein the beam of laser light penetrates the region of tissue to a depth between a surface and 6 mm.
8. The method of any of items 1-5, wherein the beam of laser light penetrates the region of tissue to a depth of at least 6 mm.
9. The method of any of items 1-5, wherein the beam of laser light penetrates the region of tissue to a full depth of a dermis layer.
10. The method of any of the preceding items, wherein the fluorescence is induced by irradiating the melanin in an image plane with radiation at a first intensity; and
    the melanin is ablated by irradiating at least a portion of the melanin in the image plane with radiation at a second intensity greater than the first intensity.
11. The method of any of the preceding items, wherein the fluorescence is induced by irradiating the melanin in an image plane with radiation at an intensity on the order of $10^5$ $W/cm^2$ to $10^7$ $W/cm^2$.
12. The method of any of the preceding items, wherein the fluorescence is induced by irradiating the melanin with radiation at a first power level; and
    the melanin is ablated by irradiating the melanin with radiation at a second power level greater than the first power level.
13. The method of any of the preceding items, wherein the step of detecting the stepwise multi-photon fluorescence includes generating a map of the detected fluorescence, the map comprising a series of image planes, each image plane comprising a pixel array in which pixels where fluorescence has been detected are identified.
14. The method of any of the preceding items, wherein:
    the step of inducing the stepwise multi-photon fluorescence comprises scanning a light source over the region of tissue,
    the step of detecting the fluorescence from the melanin in the region comprises generating a map specifying areas of the detected fluorescence in the region, and
    the step of ablating at least a portion of the melanin from which the fluorescence is detected comprises moving a light source over the region of tissue to the areas of the detected fluorescence specified in the map.

15. The method of any of the preceding items, further comprising repeating, at a new region of tissue, the steps of inducing stepwise multi-photon fluorescence in melanin, detecting the fluorescence from the melanin, and ablating at least a portion of the melanin from which the fluorescence is detected.

16. The method of any of the preceding items, further comprising monitoring fluorescence from the region after ablation to determine completion of ablation.

17. The method of any of the preceding items, wherein the fluorescence is detected at a resolution of less than 10 μm in an image plane.

18. The method of any of the preceding items, wherein the fluorescence is detected at a resolution of less than 1 μm in an image plane.

19. The method of any of the preceding items, wherein the fluorescence is detected at a resolution of less than 500 nm in an image plane.

20. The method of any of the preceding items, wherein the fluorescence is detected at a resolution of a diameter of a single grain of melanin.

21. The method of any of the preceding items, wherein the step of ablating the melanin comprises transmitting a beam of laser light from a continuous wave laser source to the region of tissue to ablate at least a portion of the melanin within the region.

22. The method of any of the preceding items, wherein a wavelength of the laser light ranges from 600 nm to 2 μm.

23. The method of any of the preceding items, wherein the beam of laser light is moved over a trajectory in an image plane to ablate at least a portion of the melanin in the image plane.

24. The method of any of the preceding items, wherein the beam of laser light is moved over multiple image planes, each image plane located at a different depth within the region of tissue, to ablate at least a portion of the melanin in each of the multiple image planes.

25. The method of any of the preceding items, wherein the beam of laser light penetrates the region of tissue to a depth between a surface and 500 μm.

26. The method of any of items 1-24, wherein the beam of laser light penetrates the region of tissue to a depth between a surface and 6 mm.

27. The method of any of items 1-24, wherein the beam of laser light penetrates the region of tissue to a depth of at least 6 mm.

28. The method of any of items 1-24, wherein the beam of laser light penetrates the region of tissue to a full depth of a dermis layer.

29. The method of any of the preceding items, wherein the melanin is ablated at a resolution of less than 10 μm in an image plane.

30. The method of any of the preceding items, wherein the melanin is ablated at a resolution of less than 1 μm in an image plane.

31. The method of any of the preceding items, wherein the melanin is ablated at a resolution of less than 500 nm in an image plane.

32. The method of any of the preceding items, wherein the melanin is ablated at a resolution of a single grain of melanin.

33. The method of any of the preceding items, wherein the step of ablating the melanin comprises ablating all the melanin in the region of tissue.

34. The method of any of the preceding items, wherein in the steps of inducing fluorescence and ablating the melanin, the region of tissue is human skin.

35. The method of any items 1-33, wherein in the steps of inducing fluorescence and ablating the melanin, the region of tissue is non-human animal skin.

36. The method of any of the preceding items, wherein, in the step of ablating the melanin, the melanin is ablated without damage to melanocytes present in the region of tissue.

37. A method of treating a melanin-related disease or condition comprising:
performing the method of item 1, wherein the region of tissue is present in a subject in need thereof.

38. The method of item 37, wherein the melanin-related disease or condition is selected from the group consisting of melanocytic lesion, congenital or acquired hyperpigmentation or melanin deposition, and other skin discoloration from melanin deposition.

39. A method of lightening skin pigmentation comprising:
performing the method of item 1, wherein the region of tissue is present in skin of a subject in need thereof.

40. A method of hair removal comprising:
performing the method of item 1, wherein the region of tissue is present in a hair shaft of a subject in need thereof.

41. A system for ablating melanin comprising:
an objective lens assembly disposed on an optical path to focus light on an image plane within a region of tissue including melanin;
a first light source disposed to transmit a first light beam on the optical path to the image plane within the region of tissue, the first light beam comprising a wavelength sufficient to induce step-wise multi-photon fluorescence of melanin in the image plane;
a detector disposed to receive a step-wise multi-photon fluorescence signal from the melanin in the image plane returning along at least a portion of the optical path; and
a second light source disposed to direct a second light beam on the optical path to the image plane within the region of tissue, the second light beam comprising a wavelength sufficient to ablate melanin in the image plane within the region of tissue.

42. The system of item 41, wherein the first light source comprises a continuous wave laser source.

43. The system of items 41-42, wherein the second light source comprises a continuous wave laser source.

44. The system of any of items 41 or 43, wherein the first light source comprises a pulsed laser source.

45. The system of any of items 41, 42 or 44, wherein the second light source comprises a pulsed wave laser source.

46. The system of any of items 41-45, wherein the wavelength of the first light beam ranges from 600 nm to 2 μm.

47. The system of any of items 41-46, wherein the wavelength of the second light beam ranges from 600 nm to 2 μm.

48. The system of any of items 41-47, wherein the first light source comprises a lower power than the second light source.

49. The system of any of items 41-48, wherein the first light source is separate from the second light source.

50. The system of any of items 41-48, wherein the first light source and the second light source comprise a single source operable at selectable power levels.

51. The system any of items 41-50, wherein the second light beam from the second light source is operable to ablate melanin at a resolution of less than 10 μm in the image plane.

52. The system of any of items 41-51, wherein the second light beam from the second light source is operable to ablate melanin at a resolution of less than 1 μm in the image plane.

53. The system of any of items 41-52, wherein the second light beam from the second light source is operable to ablate melanin at a resolution of less than 500 nm in the image plane.
54. The system of items 41-53, wherein the second light beam from the second light source is operable to ablate a single grain of melanin.
55. The system of any of items 41-54, wherein the detector comprises a photon detector.
56. The system of any of items 41-55, wherein the detector comprises a photomultiplier tube, avalanche photodiodes, a spectrometer, a CCD image array detector, or a CMOS photodiode array detector.
57. The system of any of items 41-56, further comprising a scanning system operative to scan the light beams from the first light source and the second light source across the image plane.
58. The system of any of items 41-57, wherein the scanning system comprises one or two scanning mirrors disposed to scan in orthogonal directions.
59. The system of any of items 41-57, wherein the scanning mirrors comprise one or more of a galvanometer mirror scanner or a rotating polygonal mirror scanner.
60. The system of any of items 41-59, further comprising a support disposed to support the region of tissue.
61. The system of any of items 41-60, wherein the support comprises a stage movable with respect to the image plane within the region of tissue, whereby fluorescence of melanin in multiple image planes can be induced and at least a portion of the melanin in multiple image planes can be ablated.
62. The system of any of items 41-61, wherein the objective lens assembly is movable with respect to the image plane within the region of tissue, whereby fluorescence of the melanin in multiple image planes can be induced and at least a portion of the melanin in multiple image planes can be ablated.
63. The system of any of items 41-62, further comprising one or more optical components disposed on the optical path to transmit the first light beam and the second light beam to the image plane.
64. The system of any of items 41-63, wherein the objective lens assembly and the first light source are selected to provide a light intensity at a focal area sufficient to induce fluorescence of melanin in the image plane.
65. The system of any of item 41-64, wherein the objective lens assembly and the second light source are selected to provide a light intensity at a focal area sufficient to ablate melanin in the image plane.
66. The system of any of items 41-65, further comprising a controller in communication with the objective lens assembly, the first light source, the second light source and the detector, wherein the controller is operative to store detected fluorescence signals from the melanin in the image plane and to control the second light source to ablate melanin at locations in the tissue corresponding to the detected fluorescence signals.
67. The system of any of items 41-66, wherein the controller is operative to scan the first light source over the region of tissue to induce the stepwise multi-photon fluorescence, to generate a map specifying areas of the detected fluorescence in the region, and to move the second light source to the areas of the detected fluorescence specified in the map.
68. The system of any of items 41-67, wherein the controller is operative to move the first light source to a further region of tissue, store detected fluorescence signals from the melanin in the further region, and control the second light source to ablate at least a portion of the melanin from which the fluorescence is detected in the further region.
69. The system of any of items 41-68, wherein the controller is operative to control repetition of the steps of inducing stepwise multi-photon fluorescence in melanin, detecting the fluorescence from the melanin, and ablating at least a portion of the melanin from which the fluorescence is detected at a new region of tissue.
70. The system of any of items 41-69, wherein the controller is operative to monitor fluorescence from the region after ablation to determine whether ablation has been completed.
71. The system of any of items 41-70, wherein at least the objective lens assembly and a portion of the optical path from the first light source and the second light source are housed within a hand-held device.
72. The method of item 38, wherein the melanocytic lesion is selected from the group consisting of benign nevus and malignant melanoma.
73. The method of item 38, wherein the congenital or acquired hyperpigmentation or melanin deposition is selected from the group consisting of melasma, hyperpigmentation from chronic nutritional deficiency, congenital pigment deposition, Addison's disease, McCune-Albright syndrome, sun damage, solar lentigo, deposition sun damage, ephelides, freckle, café au lait macule, nevus of Ota, nevus of Ito, post inflammatory hyperpigmentation, nevus spilus, seborrheic keratosis, blue nevus, Becker's nevus, uneven skin tone, and vitiligo.
74. The method of item 38, wherein the other skin discoloration from melanin deposition is selected from the group consisting of deposition associated with metals or mercury poisoning, and skin discoloration due to a side effect from drug usage.

DESCRIPTION OF THE DRAWINGS

The invention will be more fully understood from the following detailed description taken in conjunction with the accompanying drawings in which:

FIGS. 10A-10D are a group of images of a melanin block in which FIG. 10A is a brightfield image of the melanin block before ablation; FIG. 10B is a brightfield image after ablation of a letter Z in the melanin block; FIG. 10C is an enlarged image of the ablated area of FIG. 10B; and FIG. 10D is an SMPAF image of the melanin block after ablation;

FIGS. 15A-15D illustrate photomicrographs of a white hair and a black hair from a human subject in which FIG. 15A is a brightfield image, FIG. 15B is a confocal reflectance microscopy (CRM) image, FIG. 15C is a conventional multi-photon fluorescence microscopy (MPFM) image, and FIG. 15D is an SMPAF image with excitation wavelength of 785 nm;

DETAILED DESCRIPTION OF THE INVENTION

This application incorporates by reference the entire disclosure of U.S. Provisional Application No. 62/020,459 filed on Jul. 3, 2014, entitled "The Stepwise Multi-Photon Activated Fluorescence Guided Selective Ablation of Melanin."

The present invention provides a method and system that utilizes the stepwise multi-photon activated fluorescence (SMPAF) of melanin to guide the ablation of melanin in human or animal skin or other tissue. The method and system can be used to treat melanin-related skin diseases and conditions with a high precision. A continuous-wave (CW) laser light source can be used to induce fluorescence and provide ablation at low cost.

Figure 1:
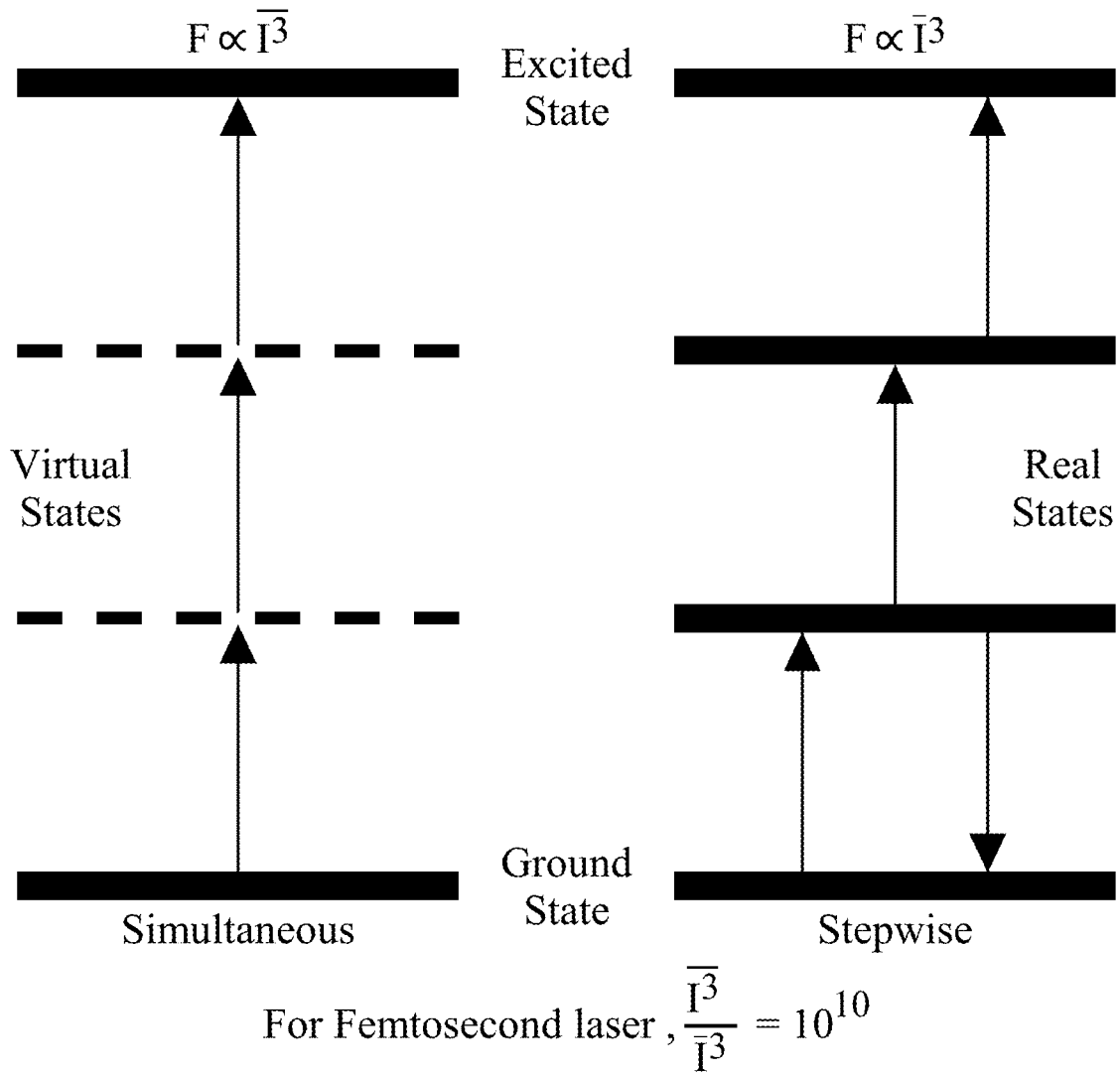
FIG. 1 is a schematic illustration of simultaneous and stepwise photon excitation.

Typically, multi-photon fluorescence involves the simultaneous absorption of photons to excite an electron from the ground state to the excited state, which requires the use of a laser pulsed for extremely short intervals, on the order of femtoseconds, at high instantaneous power to achieve a high photon flux. Fluorescence of melanin, however, can occur with a step-wise multi-photon excitation process, in which photons are absorbed individually and sequentially and the electron is excited step-wise from the ground state to an intermediate state or states before reaching the state at which fluorescence occurs. See FIG. 1.

More particularly, enhanced melanin fluorescence can be induced by a step-wise multi-photon activated fluorescence (SMPAF) process. An activation step to induce the melanin SMPAF signal can employ radiation ranging from the visible to the near infrared (NIR), from 600 nm to 2 μm. Melanin fluorescence can shift depending on the wavelength of the excitation source. In one example, using a 1505 nm laser has resulted in a peak at approximately 960 nm. Fluorescence has been activated using low laser power, with intensities on the order of $10^5$ to $10^7$ W/cm². SMPAF can also detect melanin without background interference from other biological components.

Stepwise multi-photon activated fluorescence (SMPAF) differs from simultaneous two-photon excitation of fluorescence in several ways. The step-wise process involves real intermediate excitation states, while the simultaneous process lacks real intermediate states. SMPAF can occur with excitation intensities that are two or more orders of magnitude lower than simultaneous excitation processes to obtain the same population density of fluorescence. The intensity needed to activate the multi-step fluorescence process is lower than for simultaneous fluorescence. Thus, the stepwise multi-photon activation process can employ a continuous wave (CW) laser, rather than a pulsed laser, substantially reducing the cost. The lifetimes of the intermediate states and the excited states of activated melanin is calculated and estimated using rate equations are discussed in more detail below.

Figure 2:
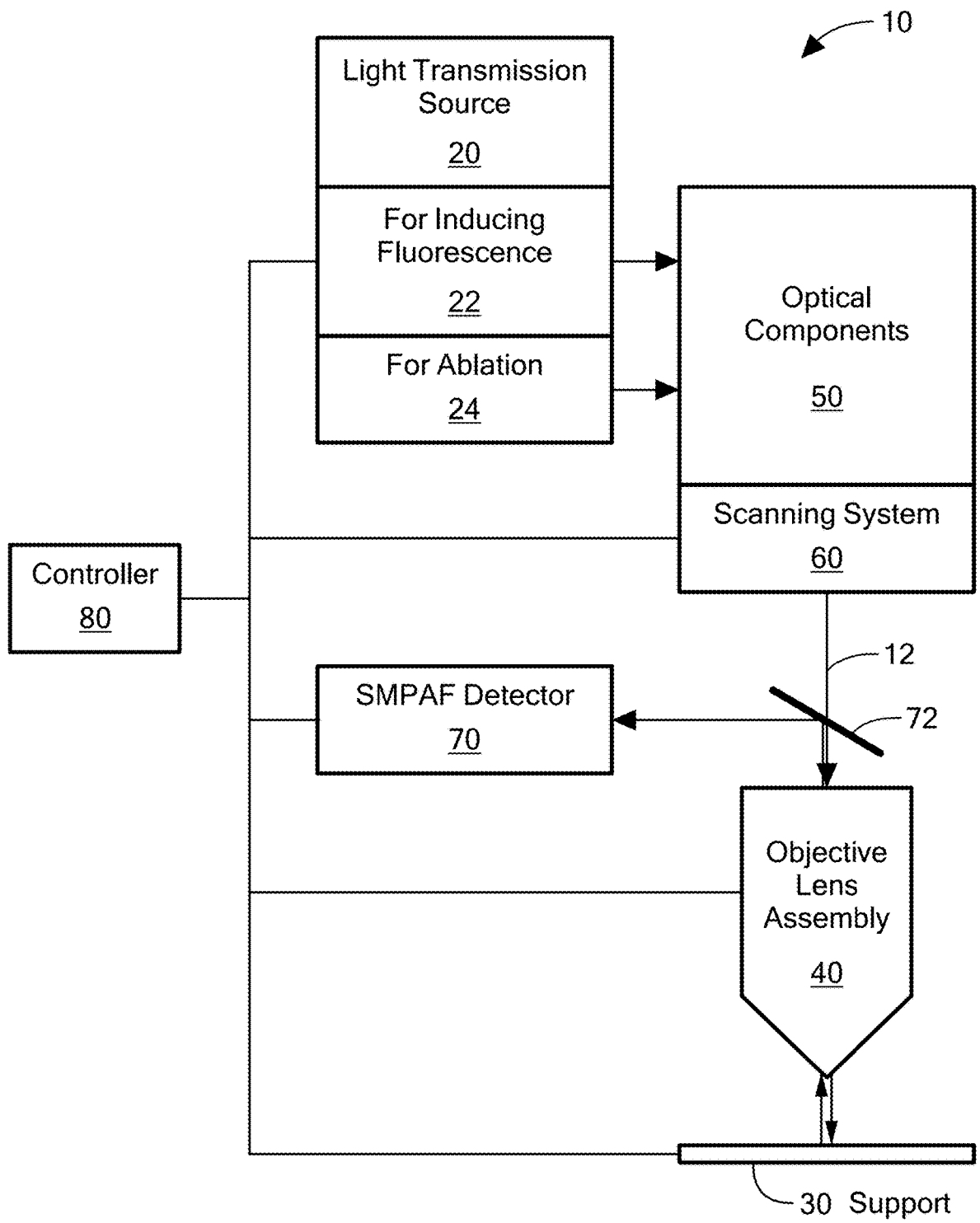
FIG. 2 is a block diagram of an embodiment of a melanin ablation system.
Figure 3:
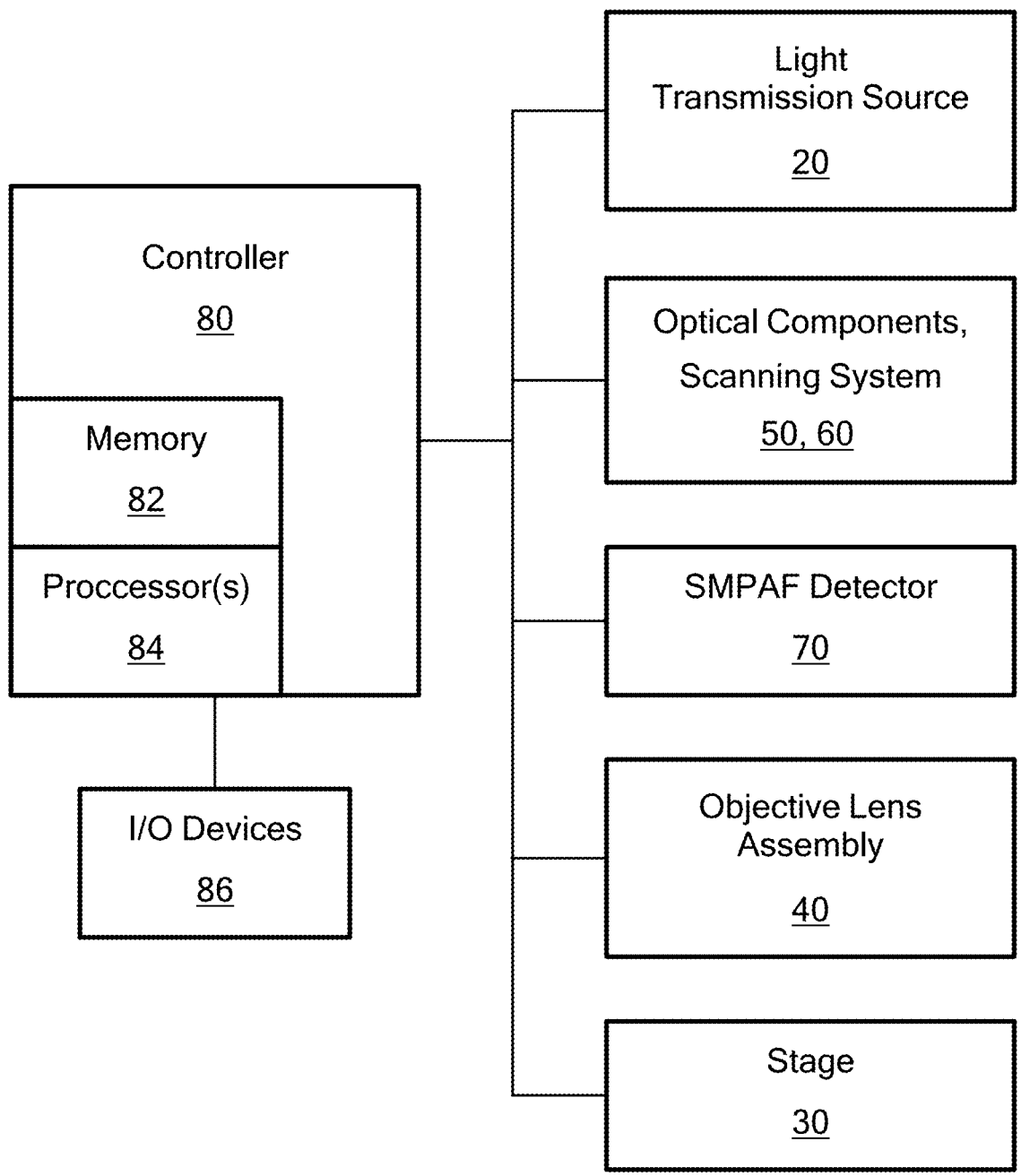
FIG. 3 is a block diagram of a controller of a melanin ablation system.

Referring to FIGS. 2-3, one embodiment of a system 10 for melanin ablation employs a light transmission source 20 operable at multiple power levels, a lower level 22 for inducing fluorescence of the melanin for detecting the location of the melanin in a sample or region of tissue, and a higher level 24 for subsequent ablation of the melanin once detected. The system also includes a support 30, such as a stage or other surface, for securely holding the sample or region of tissue containing melanin during the steps of inducing and detecting fluorescence and the subsequent ablation of melanin. An objective lens assembly 40 is provided on an optical path 12 from the light source 20 to the region of tissue to focus the light beam on an image plane within the region of tissue. Other optical components 50 can be provided on the optical path 12 for transmission of the light beam from the light source 20 to the region of tissue, depending on the configuration of the system. A scanning system 60 can be provided for scanning the light beam over the image plane. A stepwise multi-photon activated fluorescence (SMPAF) detector 70 is also provided to receive fluorescence signals emitted from melanin present in the region of tissue. A partially reflective, partially transmissive mirror 72 or beam splitter can be used to divert the fluorescence signals that travel back along the optical path to the SMPAF detector while allowing the light beam from the light source(s) to pass through to the region of tissue. A controller 80 can be provided in communication with the various system components to direct their operations.

In one embodiment, the light transmission source 20 can be a coherent or laser light source, which can comprise two separate laser sources operable at different power levels or one laser source switchable between different power levels. The or each laser source can be a continuous wave laser source or a pulsed laser. Notably, a continuous wave laser source can suitably be used for SMPAF melanin detection and ablation, as described above. Suitable wavelengths for inducing fluorescence and for ablation can range from 600 nm to 2 μm. The wavelengths of the low power source 22 and the high power source 24 can be the same or different. Laser sources can include, for example and without limitation, ruby lasers, alexandrite lasers, diode lasers, and Nd:YAG lasers. The controller 80 controls operation of both the lower power level and the higher power level sources, for example, by turning each source on or off at the appropriate times or switching power levels of a single source. In other embodiments, a non-coherent source, for example, a zenon lamp, can be used.

The objective lens assembly 40 is provided to focus the light beam on an image plane within the region of tissue. The objective lens assembly determines the focal area or resolution on the image plane. Resolution can be specified as the diameter of the focal area. In some embodiments, the objective lens can achieve a resolution in the image plane of less than 10 µm. In some embodiments, a resolution can be achieved of less than 1 µm in the image plane. In still further embodiments, a resolution can be achieved of less than 500 nm in the image plane. In still further embodiments, a resolution can be the size of a particle or grain of melanin. Melanin grain size diameters can range from 30 nm to 400 nm. Objective lens assemblies capable of achieving these resolutions are commercially available, such as, for example, some of the various CFI series objectives available from Nikon Corporation of Japan.

Figure 4:
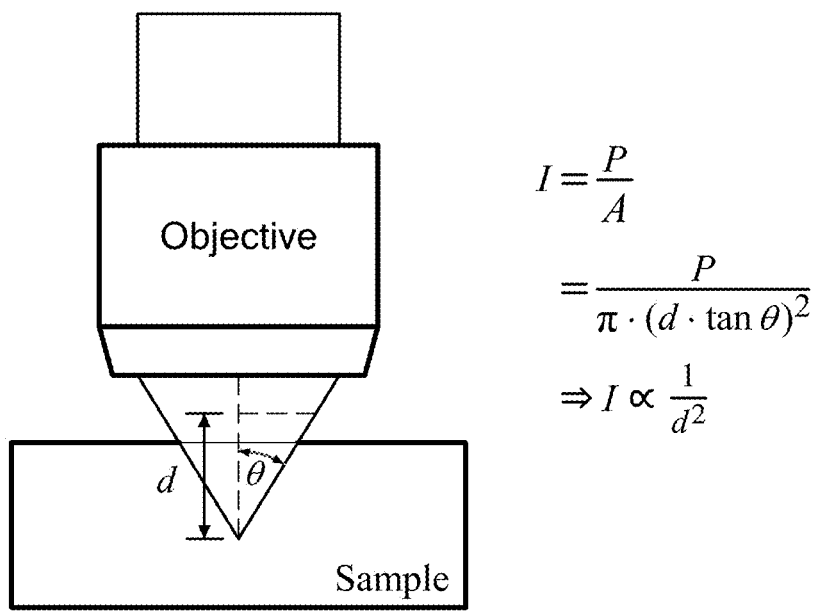
FIG. 4 is a schematic illustration of an objective lens assembly of a melanin ablation system.

The laser power necessary to induce fluorescence and subsequently ablate the melanin is determined by a laser intensity at the focal plane or image plane. Referring to the schematic illustration in FIG. 4, the intensity is the power P divided by the area A of the laser beam in any particular image plane. (FIG. 4 schematically illustrates a focal point for purposes of illustrating the intensity at a focal or image plane; it will be appreciated that, in practice, the focal point has a finite area, or resolution, in the image plane.) The light transmission source 20 and the objective lens assembly 40 can be selected, or coordinated by the controller 80, to provide a power level from the light source(s) sufficient to achieve a minimum threshold intensity for inducing fluorescence of melanin and for ablation of melanin in the image plane. With the small resolutions achievable with the objective lens assembly, the system is able to achieve intensities sufficient to ablate melanin with no or minimal collateral damage to adjacent tissue. The system also can in principle ablate melanin without damaging melanocytes. In some embodiments, the intensity can be on the order of $10^5$ to $10^7$ W/cm$^2$. Deeper penetration or thicker tissue can require a higher intensity due to energy loss.

Melanin can be present at various depths in a region of tissue, such as human or animal skin. Accordingly, the system can move the image plane to various depths. Each image plane can have a thickness (dimension in the depth dimension) ranging from 300 nm to 4 µm. Use of near infrared wavelengths by the light source(s) in particular allows a greater depth of penetration. The depth of penetration into the sample can range from the surface to the full depth of a dermis layer of skin, for example, 6 mm, or more. In some embodiments, the depth of penetration can range from the surface to 500 µm; in other embodiments, the depth of penetration can range from the surface to 6 mm. In some embodiments, the depth of penetration can be as deep as 6 mm, as deep as 7 mm, as deep as 8 mm, as deep as 9 mm, or as deep as 1 cm.

The penetration depth of the image plane can be adjusted in any suitable manner. In some embodiments, the objective lens assembly 40 can be moved or optical components within the objective lens assembly can be adjusted to move the image plane in the Z-direction within the region of tissue. In other embodiments, the system can employ as the support 30 a stage that can be moved in the depth direction (a Z-direction) each time a new image plane is to be imaged.

Various additional optical components 50 are provided on the optical path to transmit the light beam from the light source or sources to the sample containing the melanin. The optical components can include, without limitation, beam expanders; collimating lenses; telescope or relay lenses; filters, such as shortpass filters, longpass filters, and polarizing filters; mirrors, such as partially transmitting mirrors and dichroic mirrors; beam splitters; quarter wave plates; and the like, depending on the application. In some embodiments, the system can be implemented as a portable or hand-held device. A hand-held device may require the use of a more compact optical configuration than a larger stationary device or a microscope. In some embodiments, a portion of the system, such as the objective lens assembly 40 and a portion of the optical path 12 from the first and second light sources 22, 24 can be housed in a hand-held device.

The system also includes a scanning system 60, in communication with the controller 80, to provide scanning of the laser beam in the X and Y directions over the image plane. Any suitable scanning system can be used, such as two galvanometer scanners, one for scanning in the X direction and one for scanning in the Y direction. Other scanning systems can be used, such as one galvanometer mirror tiltable in both the X and Y directions, two rotating polygonal mirror arrays or a combination of a rotating polygonal mirror and galvanometer mirror. By scanning an appropriate low level laser beam across an area in an image plane containing melanin, melanin present within the area in the image plane can be induced to fluoresce.

The SMPAF detector 70 can be any suitable detector capable of detecting light in the spectrum emitted during melanin fluorescence. Any suitable photon detector can be used. Such detectors include, without limitation, a photomultiplier tube, avalanche photodiodes, a spectrometer, a CCD image array detector, or a CMOS photodiode array detector. A mirror 72, such as a partially reflecting, partially transmitting mirror or dichroic mirror, can be located in the optical path to divert the fluorescence signal from melanin to the detector. The SMPAF detector can also be in communication with the controller 80 to provide data to the controller regarding locations from which fluorescence signals are received. The controller can also be in communication with the scanning system to control the scanning and thereby map the locations of received fluorescence signals with their locations of origin within the region of tissue.

Figure 5:
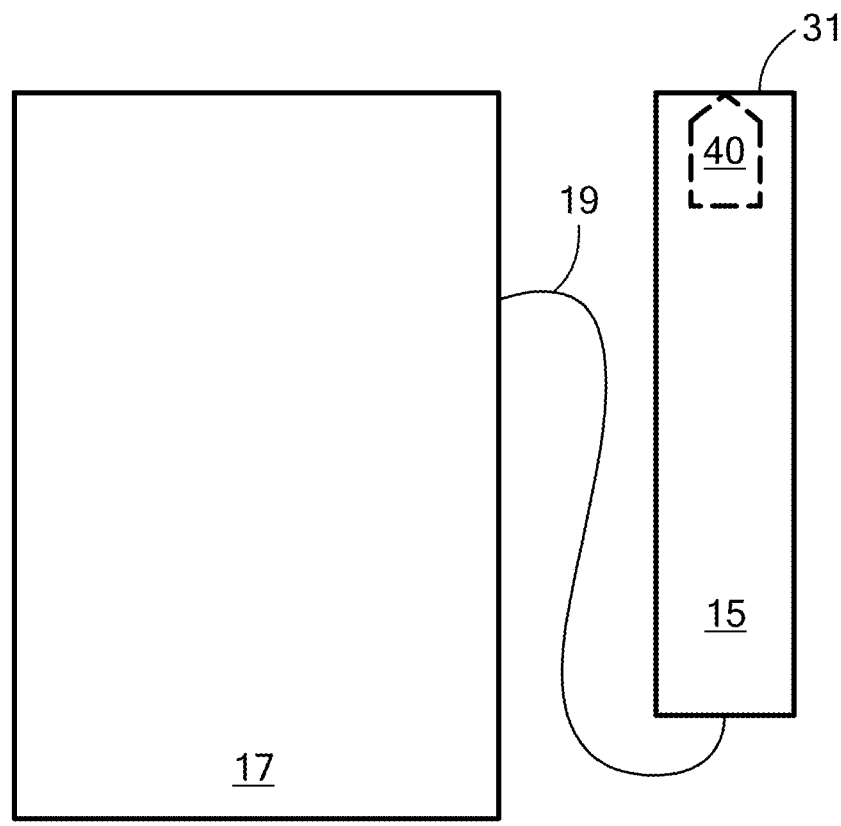
FIG. 5 is a schematic illustration of an embodiment of a hand-held device for a melanin ablation system.

In some embodiments, the system for melanin ablation can be implemented as a hand-held device. For example, referring to FIG. 5, a hand-held device can house the objective lens assembly 40 and other optical components in a housing 15. The housing can include a support surface 31 adjacent an exit of the objective lens assembly 40 to maintain the region of tissue stationary with respect to the objective lens assembly. The hand-held device can be connected via a cable 17, such as a fiber optic cable, to a base unit 17 that can house other components, such as the controller and light transmission source.

In some embodiments, the system can be implemented with a stage for supporting a sample or region of tissue. In some embodiments, the stage can be movable in two (X-Y or in-plane) dimensions parallel to the image plane. In other embodiments, the stage can be movable in three (X-Y-Z) dimensions to provide out-of-plane motion as well. Motion of the stage can be provided in any suitable manner, such as with one or more stepper motors or piezoelectric motors in communication with the controller. Any other suitable mechanical, electrical, or electromechanical components, such as gearing and linkages, can be provided to effect movement of the stage.

Figure 6:
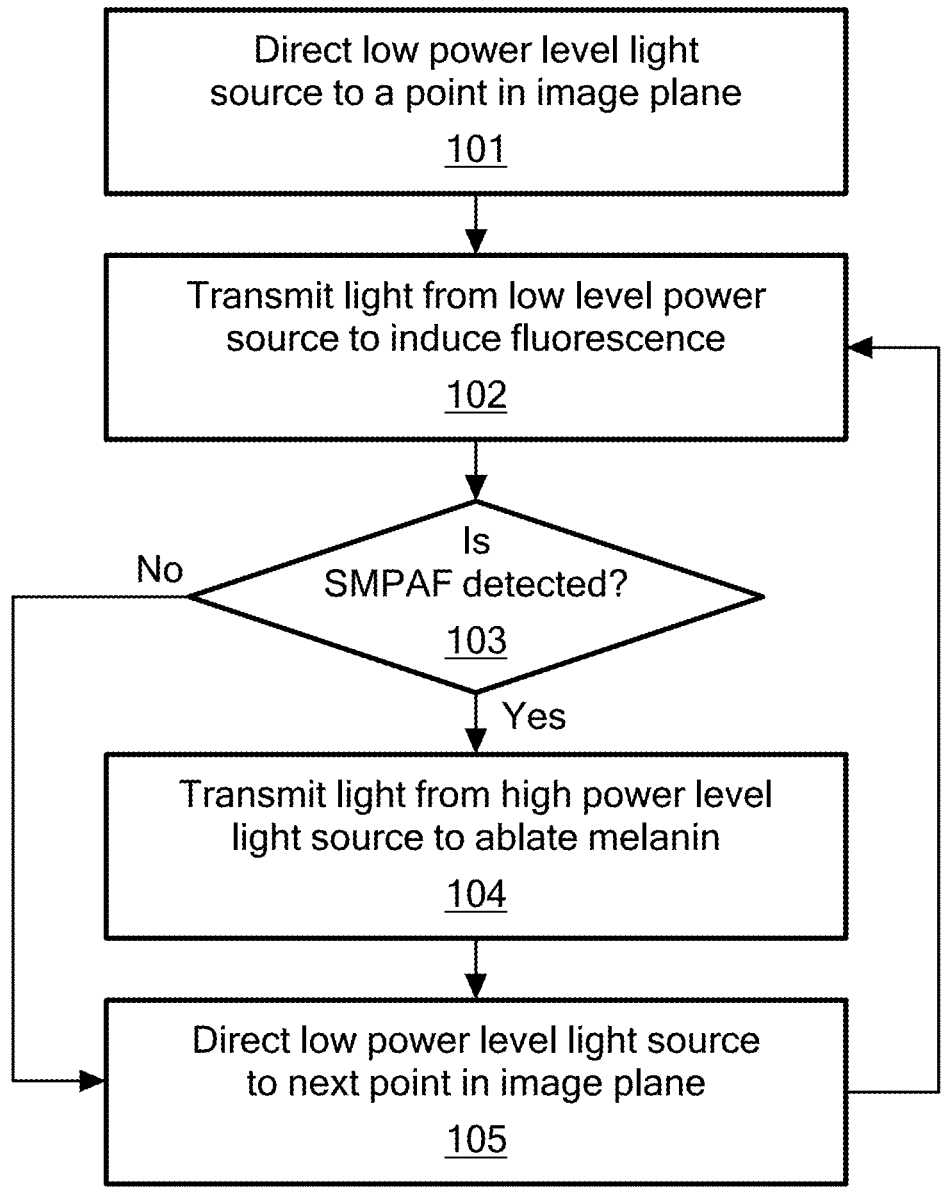
FIG. 6 is a flow chart of an embodiment of a method of melanin ablation.

FIG. 6 illustrates an embodiment of a method of melanin ablation. The low power level light source 22 is directed to a first point in an image plane (step 101) to transmit light to induce SMPAF of melanin at that point (step 102). If SMPAF is detected (step 103), then the melanin at that point is ablated using the high power level light source (step 104). The low power level light source is moved to another point in the image plane (step 105) and the inducing and detecting steps (102, 103) are repeated. If melanin is detected, the ablating step (step 104) is performed. Optionally, the system can check for SMPAF immediately after each ablation step to determine if ablation is sufficiently complete before moving to the next point in the image plane.

Figure 7:
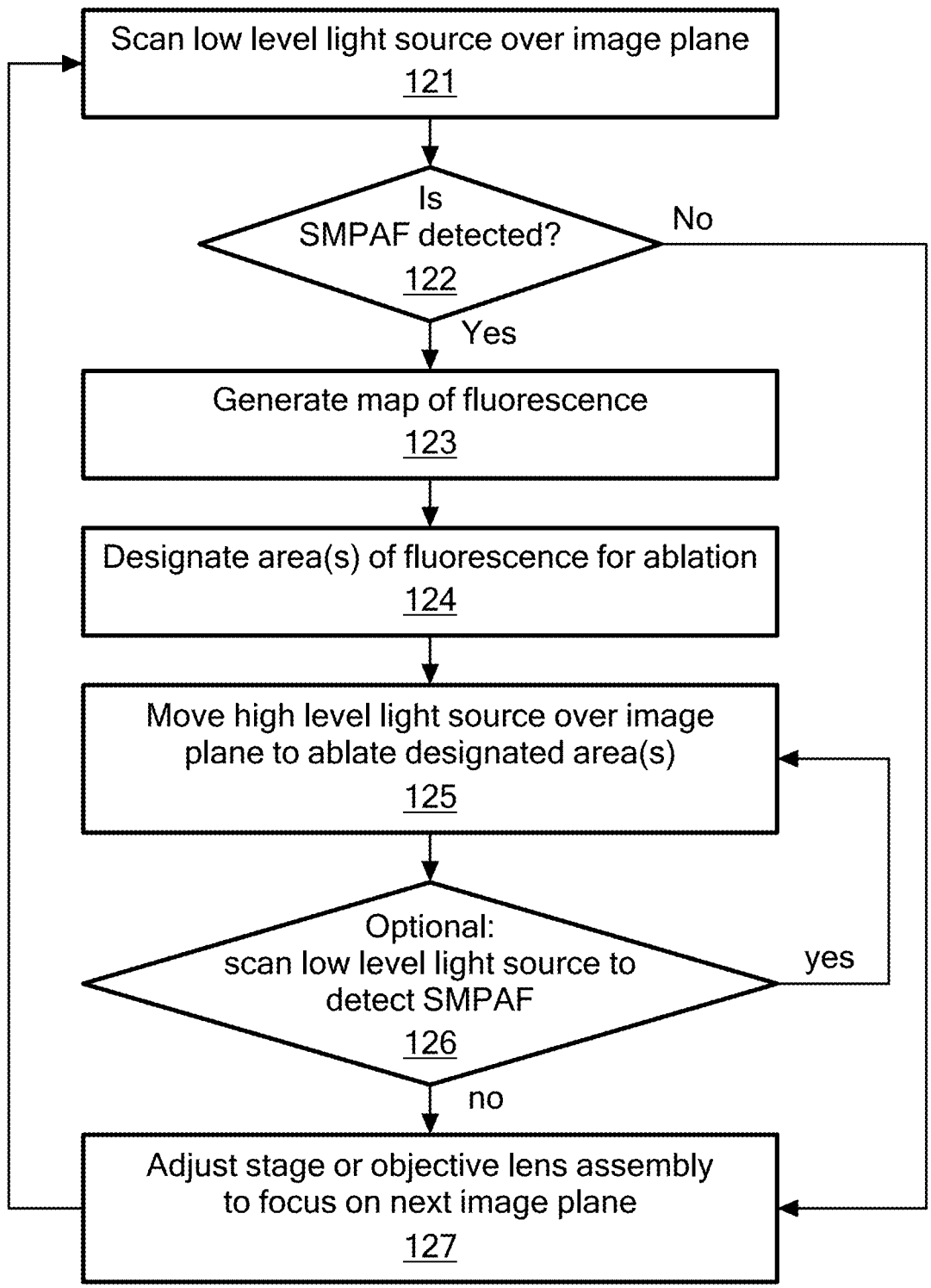
FIG. 7 is a flow chart of a further embodiment of a method of melanin ablation.

FIG. 7 illustrates a further embodiment of a method of melanin ablation. The low power level light source is scanned over an image plane (step 121), for example, in a raster pattern. If melanin is detected (step 122), a map is generated of the image plane indicating where fluorescence is detected (step 123). The map is used to designate areas of melanin ablation (step 124). Then the high power level light source is moved over the image plane to ablate melanin in the designated areas (step 125). Optionally, to monitor the ablation, the low power level light source can be scanned over the image plane again to detect SMPAF (step 126). Once ablation in the image plane is satisfactorily completed, the objective lens or stage is adjusted to move the focal area to the next image plane (step 127).

Figure 8:
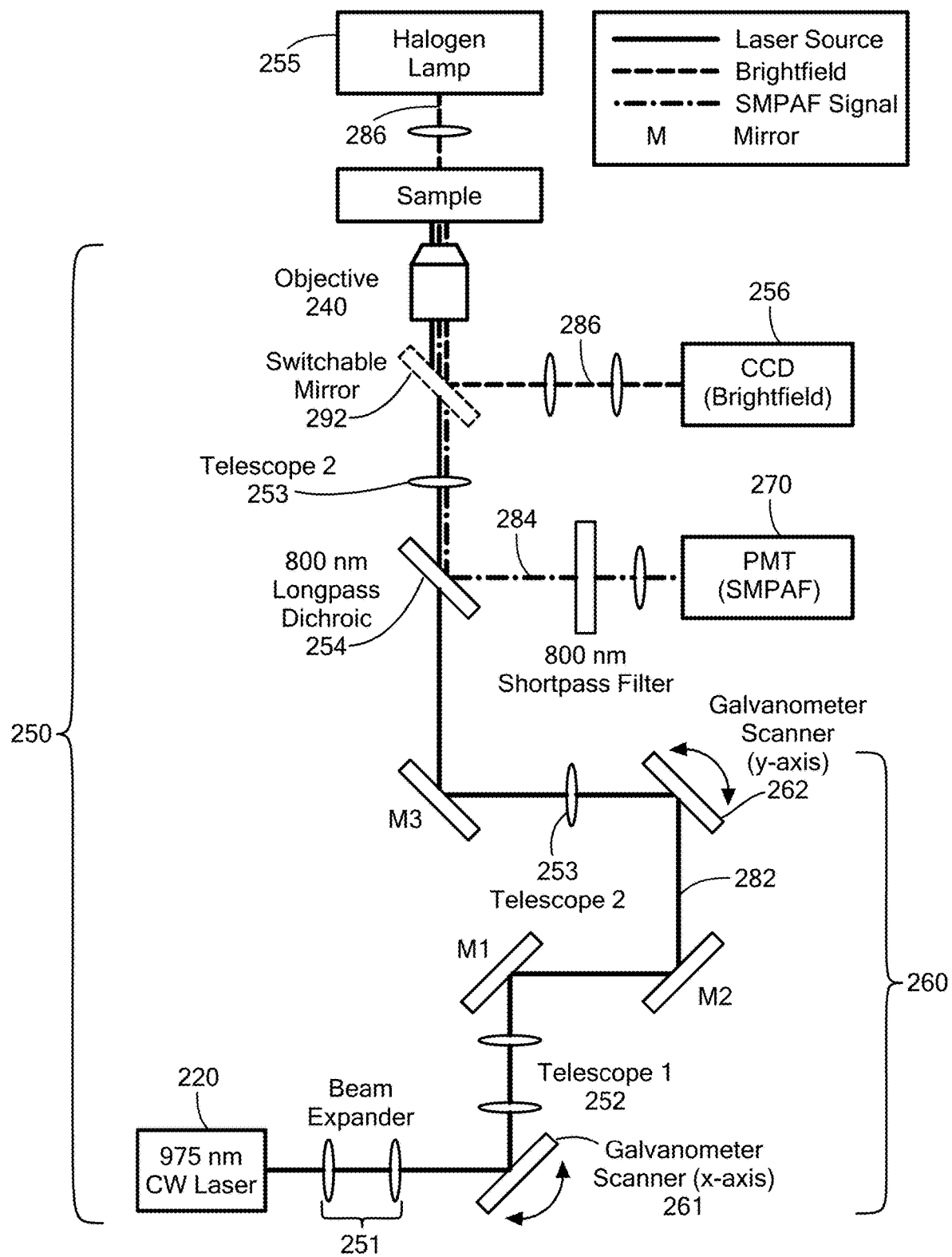
FIG. 8 is a schematic diagram of an embodiment of an optical layout of a melanin ablation system.

Referring now to FIG. 8, one embodiment of an optical layout with optical components 250 and scanning system 260 for use in a system for the detection and ablation of melanin is illustrated. This system also includes a brightfield mode for viewing a sample or region of tissue and obtaining images thereof. A continuous wave laser 220 is provided, controlled by a diode controller, to serve as the illumination source for the SMPAF (path 282). The laser beam is first expanded and collimated by a beam expander 251. A two-dimensional scanning system 260 is provided. In one embodiment, a first galvanometer scanner 261 scans the beam along the X-axis. A first telescope lens assembly 252 is used as a relay. A second galvanometer scanner 262 scans the beam along the Y-axis. A second telescope lens 253 assembly is used as a beam expander as well as a relay. A switchable mirror 272 is utilized for switching between the brightfield mode and the SMPAF mode. The SMPAF signals are collected by an objective lens system 240, and delivered to a SMPAF photomultiplier tube 270 through a longpass dichroic mirror 254 (path 284). A halogen lamp 255 serves as the illumination source of the brightfield mode (path 286). The brightfield images are collected by a camera system 256, such as a CCD camera. In this embodiment, the images reaching the camera system are mirrored images; thus, the images are mirrored again by software.

Referring to FIG. 3, the controller 80 can include memory 82 and a processing unit(s) 84 and can be in communication with various input and output devices 86 to allow an operator to use the system. For example, the controller can store in memory detected fluorescence signals from the melanin in each of the image planes and can include stored drivers or routines with instructions for controlling operation of the elements of the system.

In some embodiments, the controller 80 is operative to scan the first light source over an image plane in a region of tissue to induce the stepwise multi-photon fluorescence of melanin and to generate a map specifying areas of the detected fluorescence in the image plane. The map can be defined by, for example, a pixel array in which pixels where fluorescence has been detected are identified. The controller is further operative to move the second light source to the areas of the detected fluorescence specified in the map to ablate melanin at those locations. The second light source can be moved in any suitable pattern to ablate the melanin. The controller is operative to move the first light source over a further region of tissue to induce fluorescence, store detected fluorescence signals from the melanin in the further region, and control the second light source to ablate at least a portion of the melanin from which the fluorescence is detected in the further region. The further region of tissue can be an image plane located at a different depth in the region of tissue, in which case the controller can be operative to adjust the objective lens assembly or the stage.

In some embodiments, the controller is operative to monitor the fluorescence signal from the region after ablation to determine whether ablation is complete. In some applications, such as skin lightening, it may not be necessary to ablate all of the melanin detected in the region. The controller can be operative to control the amount of melanin ablated, for example, by ablating a predetermined percentage of detected melanin or by monitoring the amount of melanin detected after ablation.

The controller can be part of a computer system that executes programming for controlling the system for ablating melanin as described herein. The computing system can be implemented as or can include a computing device that includes a combination of hardware, software, and firmware that allows the computing device to run an applications layer or otherwise perform various processing tasks. Computing devices can include without limitation personal computers, work stations, servers, laptop computers, tablet computers, mobile devices, hand-held devices, wireless devices, smartphones, wearable devices, embedded devices, microprocessor-based devices, microcontroller-based devices, programmable consumer electronics, mini-computers, main frame computers, and the like.

The computing device can include a basic input/output system (BIOS) and an operating system as software to manage hardware components, coordinate the interface between hardware and software, and manage basic operations such as start up. The computing device can include one or more processors and memory that cooperate with the operating system to provide basic functionality for the computing device. The operating system provides support functionality for the applications layer and other processing tasks. The computing device can include a system bus or other bus (such as memory bus, local bus, peripheral bus, and the like) for providing communication between the various hardware, software, and firmware components and with any external devices. Any type of architecture or infrastructure that allows the components to communicate and interact with each other can be used.

Processing tasks can be carried out by one or more processors. Various types of processing technology can be used, including a single processor or multiple processors, a central processing unit (CPU), multicore processors, parallel processors, or distributed processors. Additional specialized processing resources such as graphics (e.g., a graphics processing unit or GPU), video, multimedia, or mathematical processing capabilities can be provided to perform certain processing tasks. Processing tasks can be implemented with computer-executable instructions, such as application programs or other program modules, executed by the computing device. Application programs and program modules can include routines, subroutines, programs, drivers, objects, components, data structures, and the like that perform particular tasks or operate on data.

The computing device includes memory or storage, which can be accessed by the system bus or in any other manner. Memory can store control logic, instructions, and/or data. Memory can include transitory memory, such as cache memory, random access memory (RAM), static random access memory (SRAM), main memory, dynamic random access memory (DRAM), and memristor memory cells. Memory can include storage for firmware or microcode, such as programmable read only memory (PROM) and erasable programmable read only memory (EPROM). Memory can include non-transitory or nonvolatile or persistent memory such as read only memory (ROM), hard disk drives, optical storage devices, compact disc drives, flash drives, floppy disk drives, magnetic tape drives, memory chips, and memristor memory cells. Non-transitory memory can be provided on a removable storage device. A computer-readable medium can include any physical medium that is capable of encoding instructions and/or storing data that can be subsequently used by a processor to implement embodiments of the method and system described herein. Physical media can include floppy discs, optical discs, CDs, mini-CDs, DVDs, HD-DVDs, Blu-ray discs, hard drives, tape drives, flash memory, or memory chips. Any other type of tangible, non-transitory storage that can provide instructions and/or data to a processor can be used in these embodiments.

The computing device can include one or more input/output interfaces for connecting input and output devices to various other components of the computing device. Input and output devices can include, without limitation, keyboards, mice, joysticks, microphones, displays, monitors, scanners, speakers, and printers. Interfaces can include universal serial bus (USB) ports, serial ports, parallel ports, game ports, and the like.

The computing device can access a network over a network connection that provides the computing device with telecommunications capabilities. Network connection enables the computing device to communicate and interact with any combination of remote devices, remote networks, and remote entities via a communications link. The communications link can be any type of communications link, including without limitation a wired or wireless link. For example, the network connection can allow the computing device to communicate with remote devices over a network, which can be a wired and/or a wireless network, and which can include any combination of intranet, local area networks (LANs), enterprise-wide networks, medium area networks, wide area networks (WANs), the Internet, or the like. Control logic and/or data can be transmitted to and from the computing device via the network connection. The network connection can include a modem, a network interface (such as an Ethernet card), a communication port, a PCMCIA slot and card, or the like to enable transmission of and receipt of data via the communications link.

The computing device can include a browser and a display that allow a user to browse and view pages or other content served by a web server over the communications link. A web server, server, and database can be located at the same or at different locations and can be part of the same computing device, different computing devices, or distributed across a network. A data center can be located at a remote location and accessed by the computing device over a network. The computer system can include architecture distributed over one or more networks, such as, for example, a cloud computing architecture.

Example 1

Figure 9A:
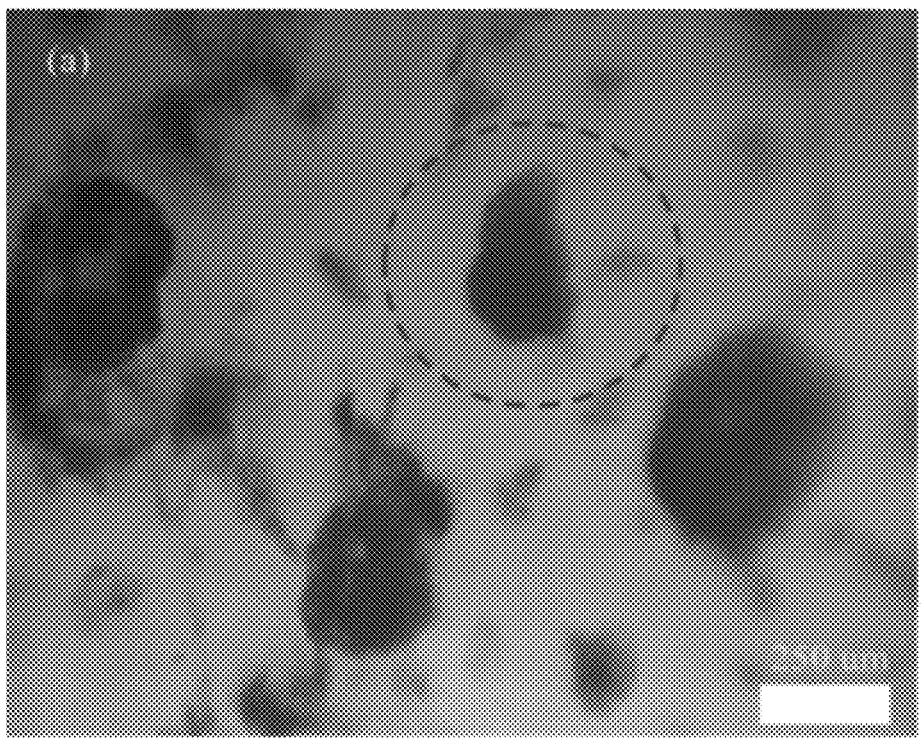
FIG. 9A is a brightfield image of a melanin block in sepia skin before ablation.
Figure 9B:
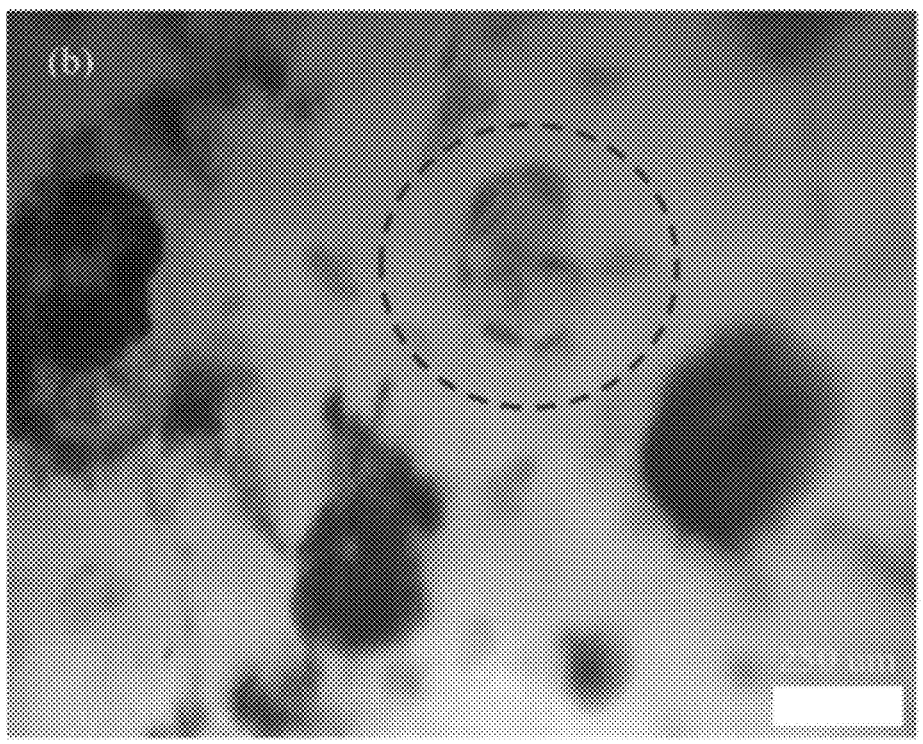
FIG. 9B is a brightfield image of the melanin block of FIG. 9A after ablation.

In one example, using an optical layout substantially as indicated in FIG. 8, a sepia sample was obtained from a piece of squid skin. The laser source was a 975 nm CW laser. The sample was placed between a cover glass and a microscope slide. FIG. 9A is a photomicrograph of a region of the sample showing several melanin blocks. One of the melanin blocks was fully ablated in one image plane, as shown in FIG. 9B. The laser power used to ablate the melanin block was estimated to be 39.2 mW. Note that only the melanin in the image plane has been ablated; to ablate all the melanin in this block, the image plane would need to be moved vertically with respect to the melanin block.

Example 2

Figure 10A:
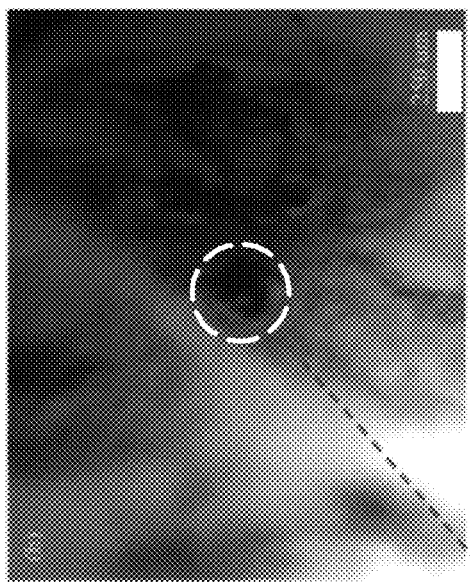
Figure 10B:
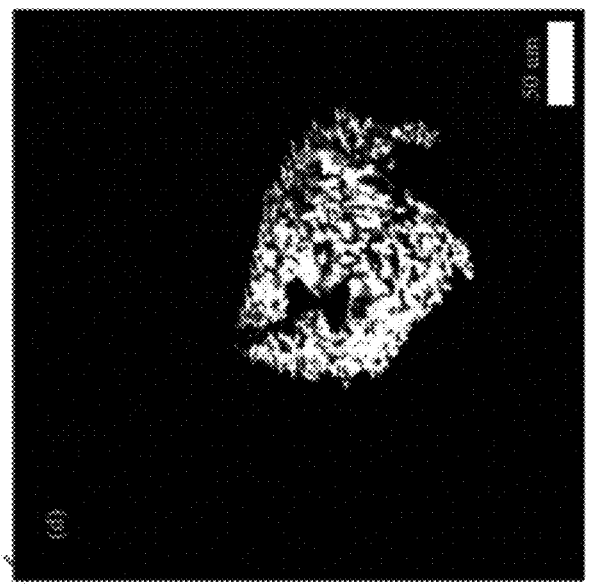
Figure 10C:
Figure 10D:
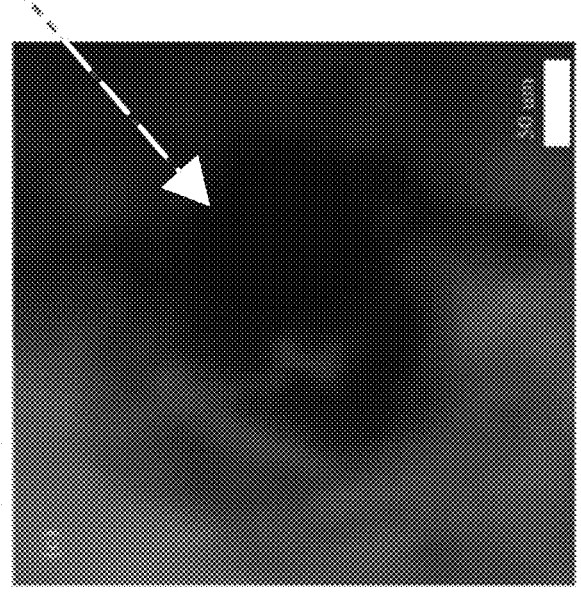
Figure 11:
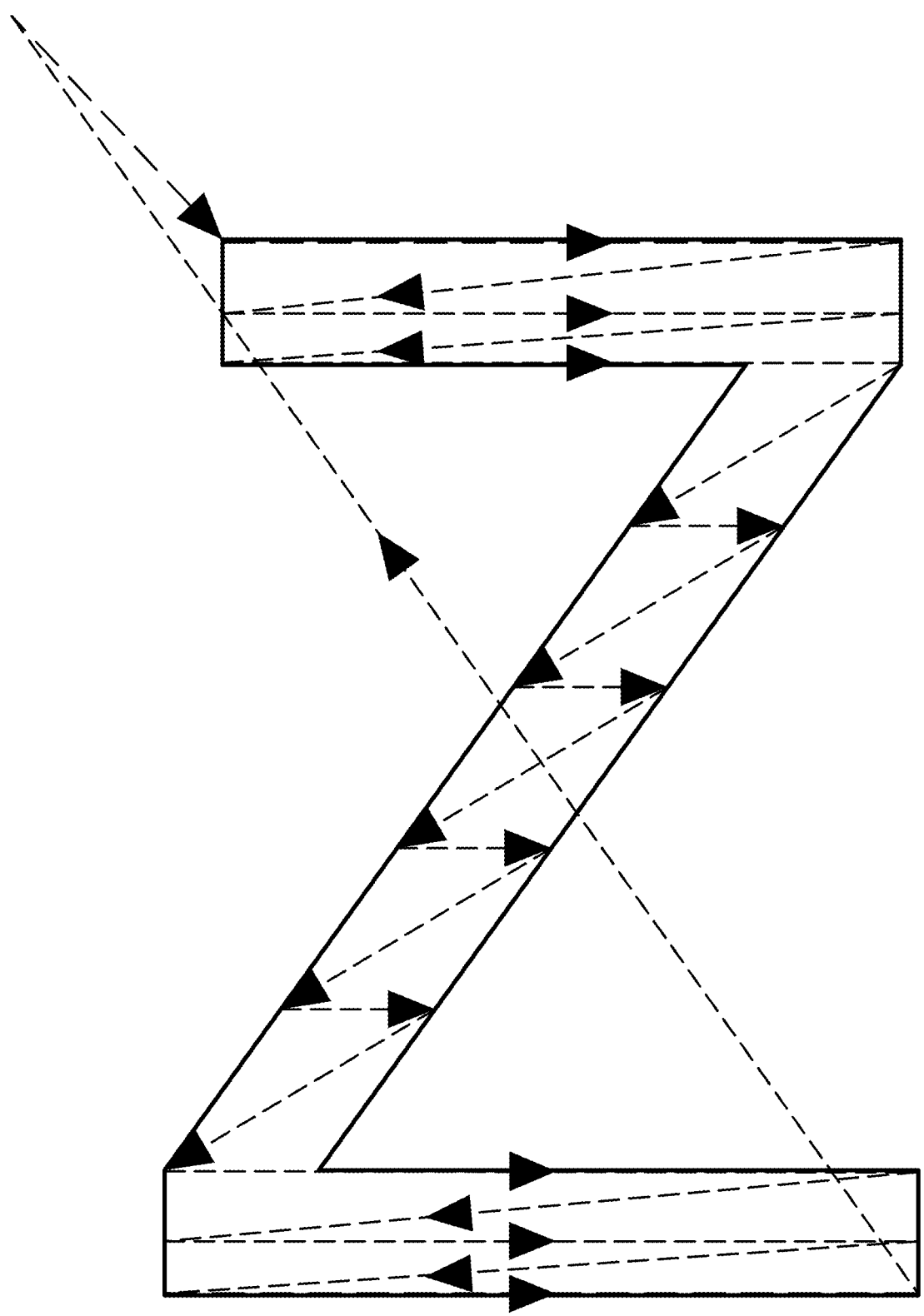
FIG. 11 is a schematic illustration of an ablation pattern for the letter Z in FIG. 10.

In a further example, micrometer resolution of melanin ablation was demonstrated by performing a partial ablation of a melanin block. FIGS. 10A-10D are a group of photomicrographs illustrating a block of melanin before and after ablation. The sample containing the melanin was obtained from a piece of squid skin. The letter "Z" having dimensions 25×35 μm was ablated in a melanin block. FIG. 10A is a brightfield image of the sepia skin before ablation. FIG. 10B is a brightfield image of the same location after ablation. FIG. 10C is an enlarged image of the circled area in FIG. 10B. FIG. 10D is a SMPAF image of the circulate area after ablation. The ablated letter Z is best seen in FIG. 10D. The laser power used to ablate the melanin was estimated to be 62.98 mW. The laser trajectory used to ablate the letter Z is illustrated in FIG. 11.

Example 3

Figure 12A:
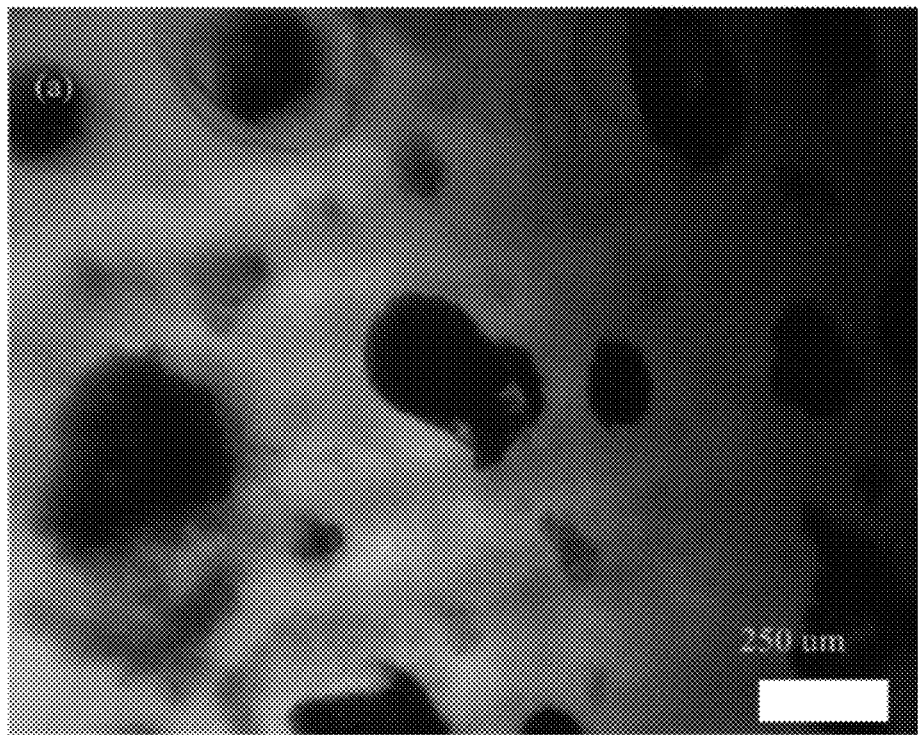
FIG. 12A is a brightfield image of a melanin block before ablation.
Figure 12B:
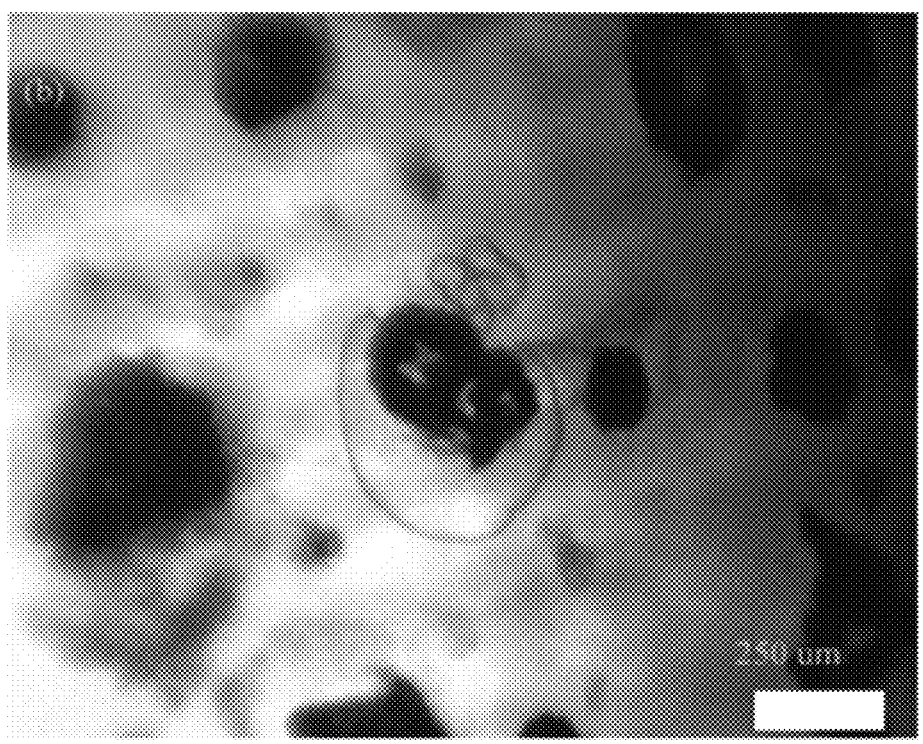
FIG. 12B is a brightfield image of the melanin block of FIG. 12A after the letters Z and L have been ablated in the melanin block, each letter having a size of ~40×50 μm.

In a still further example, a partial ablation was performed on a melanin block to further demonstrate micrometer resolution. The letters Z and L were ablated in a block of melanin in a sepia skin from a squid. FIG. 12A is a brightfield image of the sepia skin before laser ablation. FIG. 12B is a brightfield image of the same location after laser ablation. The letters Z and L, each of ~40×50 m in size, were created by partially ablating the melanin block at the center. The laser power at the sample was measured to be 34.5 mW.

Figure 13:
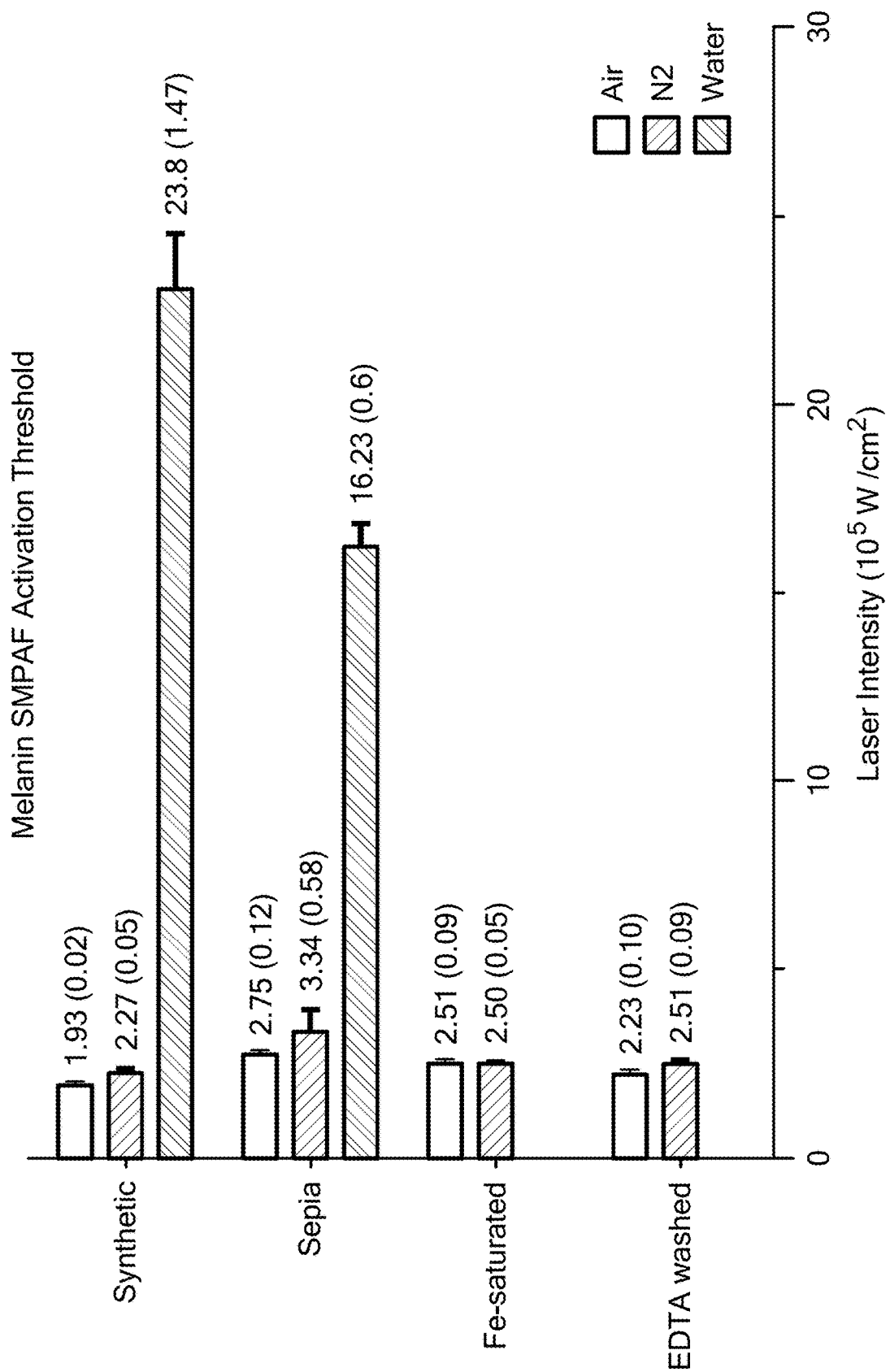
FIG. 13 is a comparison of melanin SMPAF activation threshold in air, nitrogen, and water for synthetic eumelanin, sepia eumelanin, Fe-saturated melanin, and EDTA washed (iron removed) melanin.
Figure 14A:
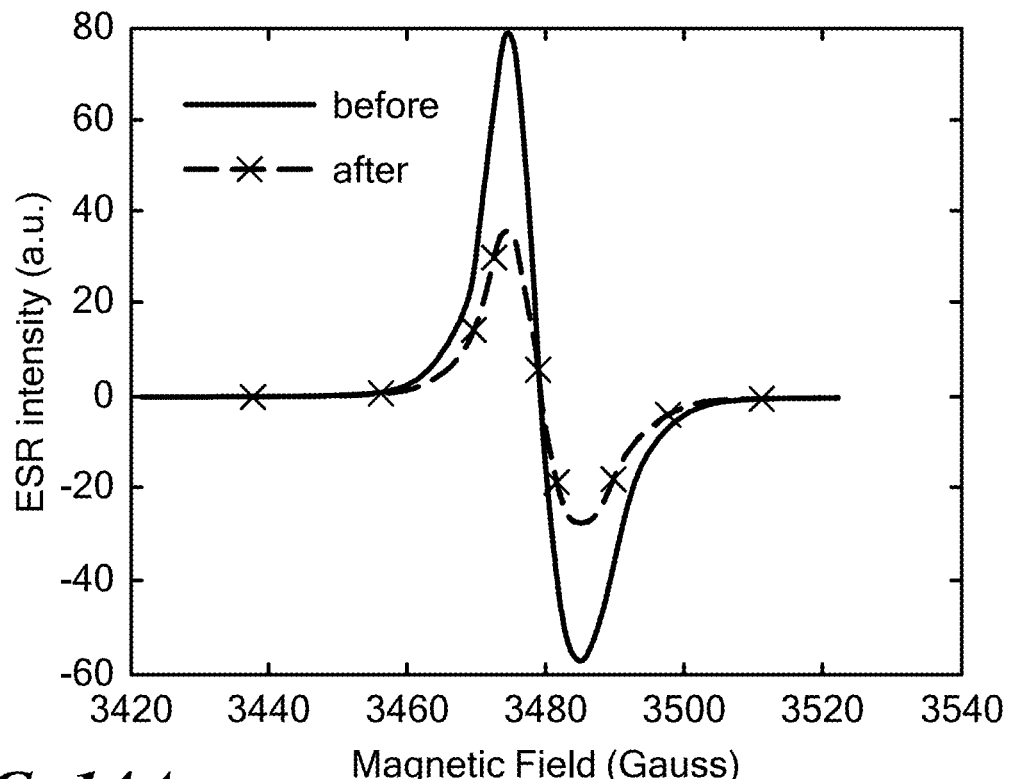
FIGS. 14A-14B are graphs of (a) melanin EPR signals before and after activation, and (b) normalization of the EPR signals of (a)
Figure 14B:
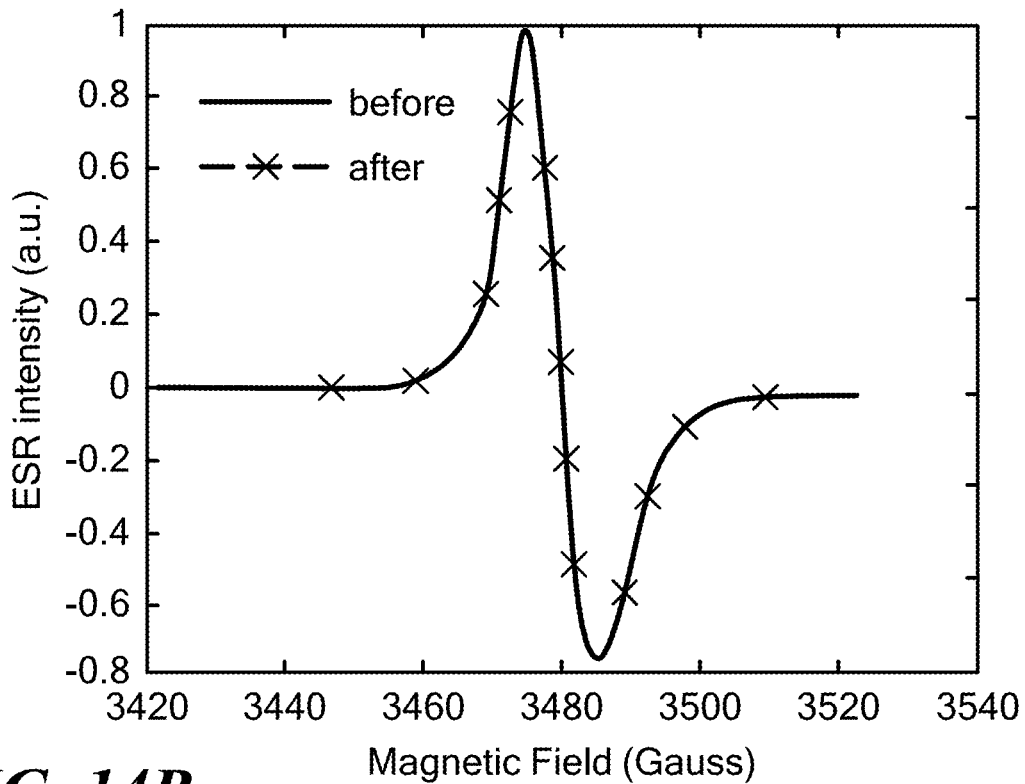

Various additional details regarding the SMPAF process are described by reference to FIGS. 13, 14A, 14B, 15A-15D, 16A, 16B, and 18. Regarding the activation process, a large photon density above the activation threshold is used to activate melanin SMPAF. The activation threshold of melanin SMPAF can vary by the type of melanin as well as the surrounding environment. In some embodiments, the activation threshold is on the order of $10^5$ to $10^6$ W/cm$^2$. After activation, SMPAF signals can be detected below the activation threshold. Thus, the laser power can be decreased after activation for purposes of detecting melanin. Melanin SMPAF can be activated and excited using either pulsed or CW lasers. The activation time can vary among melanin particles. In some embodiments, the activation time can be less than 60 s. The average activation time decreases as laser power increases. The activation threshold of various types of melanin was compared, as indicated in FIG. 13. The activation threshold was determined by increasing the input laser power step by step, with a pause of at least 1 min at each step, until SMPAF signals were detected.

The activation of melanin SMPAF may be caused in part by the dissociation of metal ions or the selective degradation of iron-containing melanin. A comparison of melanin electron paramagnetic resonance (EPR, also known as electron spin resonance (ESR)) of melanin before and after activation was performed. See FIGS. 14A, 14B. The intensity of the EPR signal decreased after activation, while the shapes of the signals remained the same. This comparison indicates those free radicals were removed from the melanin during the activation step.

Figure 15A:
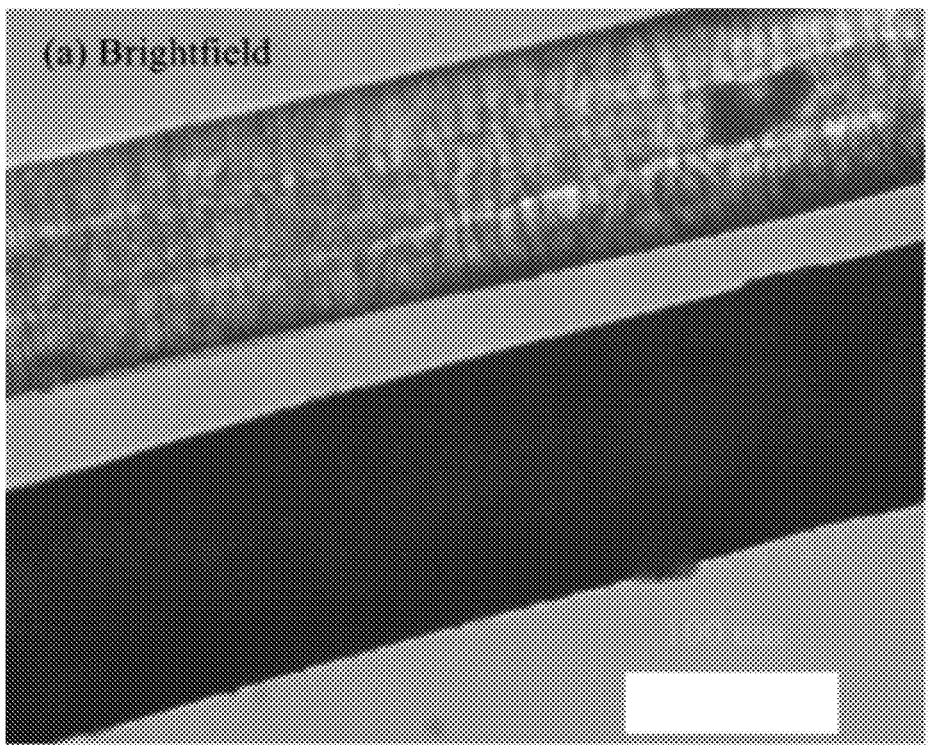
Figure 15B:
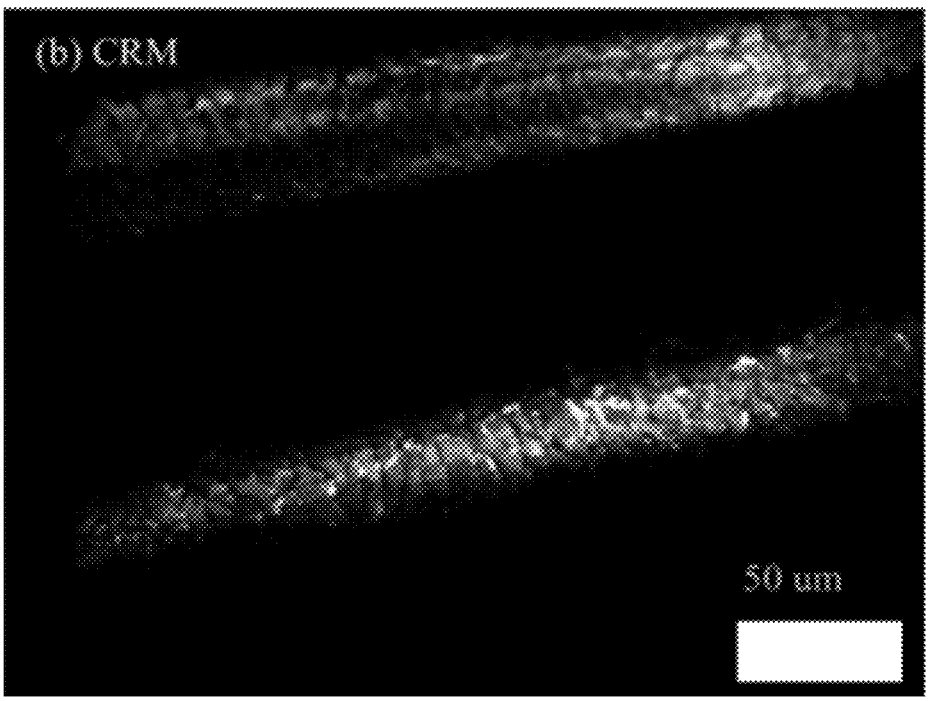
Figure 15C:
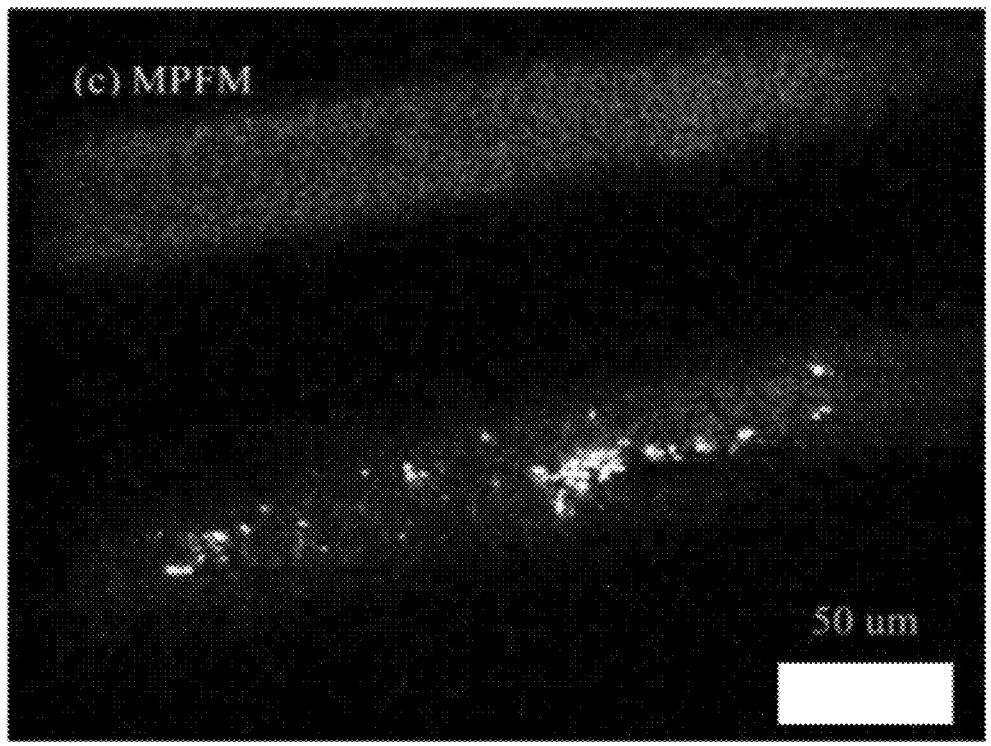
Figure 15D:
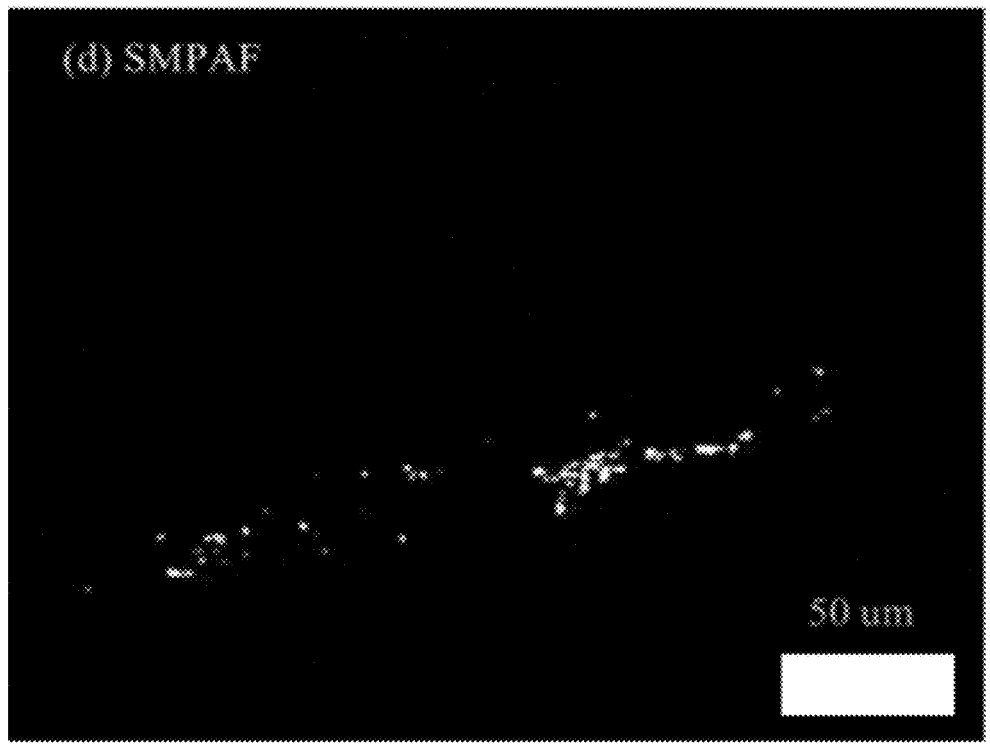

Many biological components emit auto-fluorescence under a pulsed laser, causing background signals. Melanin, however, emits SMPAF signals under the activation process described herein, which provides for a high specificity in detecting melanin in skin compared to other biological components. FIGS. 15A-15D illustrate several photomicrographs of a white hair and a black hare from a human subject. In the brightfield image, FIG. 15A, the white hair and the black hair are readily distinguishable, although melanin cannot be detected. The confocal reflectance microscopy (CRM) image, FIG. 15B, provides details of the physical structure, but melanin also cannot be detected. The conventional multi-photon fluorescence microscopy (MPFM) image, FIG. 15C, provides fluorescence signals from both melanin and other biological components. The SMPAF image, FIG. 15D, shows fluorescence signals from melanin with high specificity while lacking background signals from other biological components.

Stepwise Excitation vs. Simultaneous Excitation

As mentioned previously in this chapter, the commonly known multi-photon fluorescence is usually a simultaneous excitation process, whereas the multi-photon activated fluorescence of melanin is a stepwise excitation process, which is similar to the simultaneous excitation process, except that all the intermediate states between the excited state and the ground state are real states. In simultaneous excitation, lifetime of the virtual states is estimated to be ~$10^{-16}$ s. The lifetime of the real states are much longer (usually ~$10^{-9}$ s).

Figures 16A, 16B:
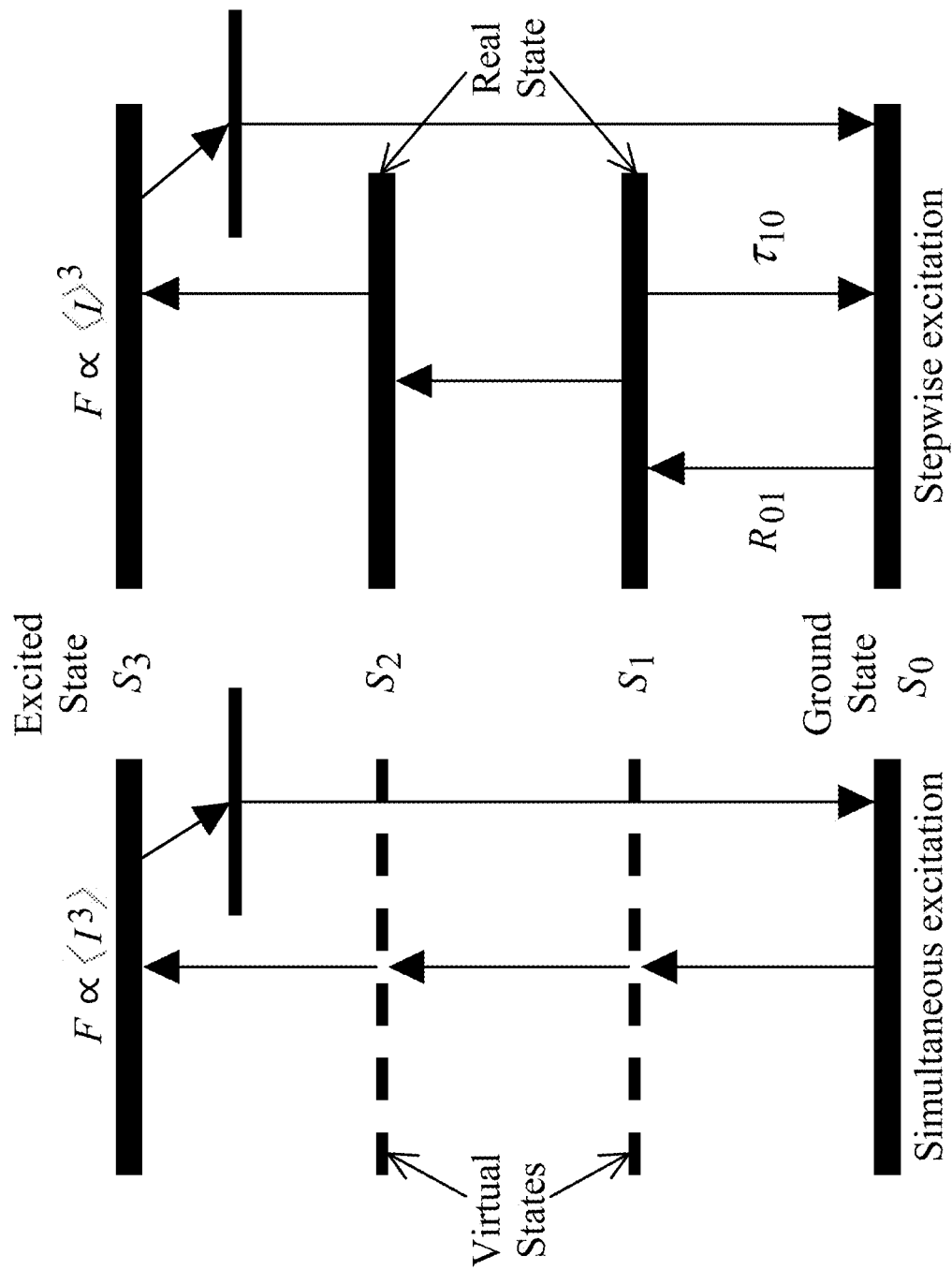
FIGS. 16A-16B are schematic illustrations of an energy diagram demonstrating in FIG. 16A simultaneous excitation, and in FIG. 16B stepwise excitation using three-photon excitation as an example.

The energy diagrams shown in FIGS. 16A and 16B follow the rate equations below:

$$\frac{d}{dt}N_1 = R_{01} \cdot I(t) \cdot (N_0 - N_1) - R_{12} \cdot I(t) \cdot (N_1 - N_2) - \frac{N_1}{T_1}, \quad \text{Equation 1}$$

$$\frac{d}{dt}N_2 = R_{12} \cdot I(t) \cdot (N_1 - N_2) - R_{23} \cdot I(t) \cdot (N_2 - N_3) - \frac{N_2}{T_2}, \quad \text{Equation 2}$$

$$\frac{d}{dt}N_3 = R_{23} \cdot I(t) \cdot (N_2 - N_3) - R_3 \cdot I(t) \cdot N_3 - \frac{N_3}{T_3}, \quad \text{Equation 3}$$

where $N_0$, $N_1$, $N_2$, and $N_3$ are the electron population density of State 0 (ground state), 1, 2, and 3 (excited state) respectively. Here, we suppose $N_0$ is constant. $R_{01}$, $R_{12}$, and $R_{23}$ are the transition rates from State 0 to State 1, State 1 to State 2, and State 2 to State 3 respectively. $R_3$ is the decay rate of the excited state. $T_1$, $T_2$, and $T_3$ are the lifetime of State 1, 2, and 3 respectively. $I(t)$ is the intensity of the input laser.

To populate electrons from State 0 to State 3, we need to have:

$$N_0 \gg N_1 \gg N_2 \gg N_3. \quad \text{Equation 4}$$

Therefore, Equation 1-Equation 3 can be simplified as:

$$\frac{d}{dt}N_1 = R_{01} \cdot I(t) \cdot N_0 - \frac{N_1}{T_1}, \quad \text{Equation 5}$$

$$\frac{d}{dt}N_2 = R_{12} \cdot I(t) \cdot N_1 - \frac{N_2}{T_2}, \quad \text{Equation 6}$$

$$\frac{d}{dt}N_3 = R_{23} \cdot I(t) \cdot N_2. \quad \text{Equation 7}$$

a) Pulsed Laser

Figure 17:
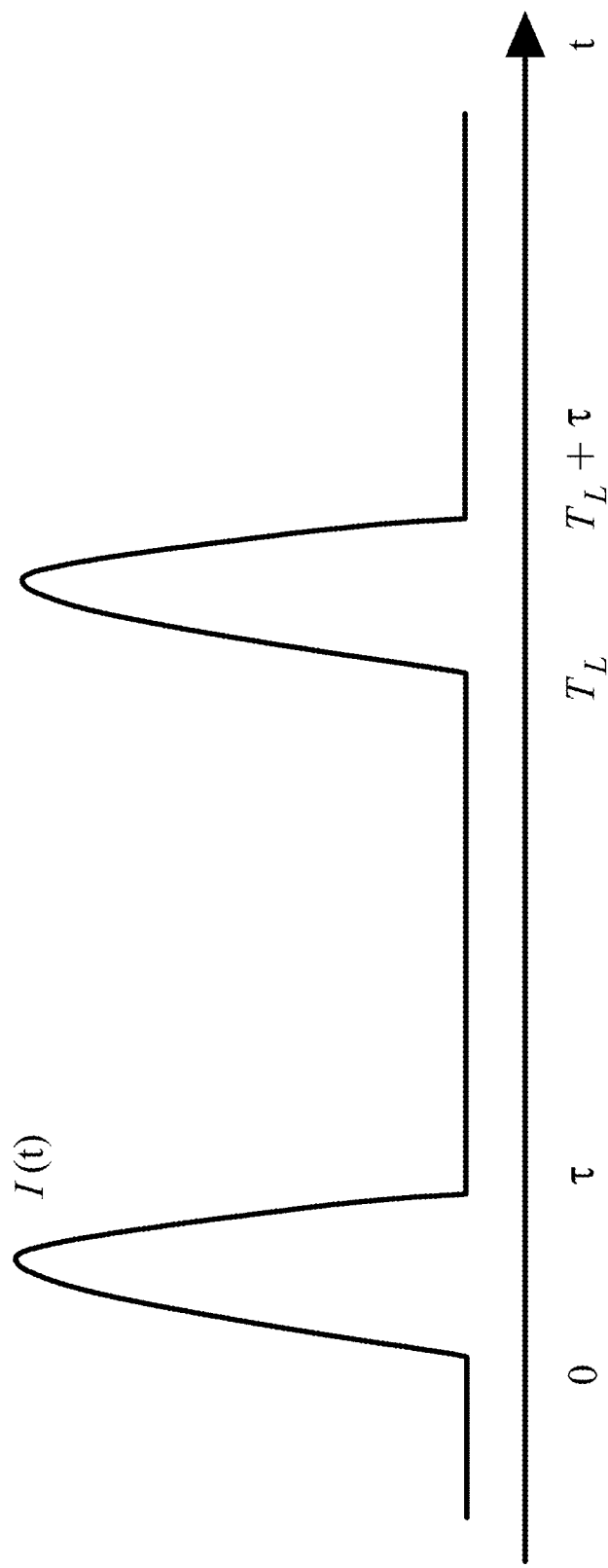
FIG. 17 is a schematic profile of a pulsed laser, in which T is the pulse width and $T_L$ is the period.

Suppose the input laser is a pulsed laser, with pulse width $\tau$, period $T_L$, and intensity $I(t)$ as shown in FIG. 17.

i) Simultaneous Excitation

The pulse width of an exemplary laser (for example, a Tsunami laser from Spectra Physics) is ~$10^{-13}$ s, which is much longer than the lifetime of virtual states, but shorter than that of the excited states (usually ~$10^{-9}$ s). Then we have $$T_1, T_2 \ll \tau \ll T_3. \quad \text{Equation 8}$$

At $t \in (0, \tau)$, $I(t) \gg 0$, from Equation 5, we have:

$$N_1 = C_1 \cdot e^{-\frac{t}{T_1}} + R_{01} \cdot N_0 \cdot e^{-\frac{t}{T_1}} \cdot \int e^{\frac{t}{T_1}} \cdot I(t) \cdot dt, \quad \text{Equation 9}$$

where $C_1$ is a constant.

Since $$\int e^{\frac{t}{T_1}} \cdot I(t) \cdot dt = T_1 \cdot e^{\frac{t}{T_1}} \cdot I(t) - T_1 \cdot \int e^{\frac{t}{T_1}} d[I(t)], \quad \text{Equation 10}$$

we have $$N_1 = C_1 \cdot e^{-\frac{t}{T_1}} + R_{01} \cdot N_0 \cdot T_1 \cdot I(t) - R_{01} \cdot N_0 \cdot T_1 \cdot e^{-\frac{t}{T_1}} \cdot \int e^{\frac{t}{T_1}} d[I(t)] \approx R_{01} \cdot N_0 \cdot T_1 \cdot I(t). \quad \text{Equation 11}$$

Here, as from Equation 8, $T_1 \ll \tau$, hence $$C_1 \cdot e^{-\frac{t}{T_1}} \approx 0.$$

To prove that $$R_{01} \cdot N_0 \cdot T_1 \cdot I(t) \gg R_{01} \cdot N_0 \cdot T_1 \cdot e^{-\frac{t}{T_1}} \cdot \int e^{\frac{t}{T_1}} d[I(t)], \quad \text{Equation 12}$$

we need to prove $$I(t) \gg e^{-\frac{t}{T_1}} \cdot \int e^{\frac{t}{T_1}} d[I(t)], \quad \text{Equation 13}$$

which is to prove $$I(t) \cdot e^{\frac{t}{T_1}} \gg \int e^{\frac{t}{T_1}} \cdot \frac{d[I(t)]}{dt} \cdot dt. \quad \text{Equation 14}$$

Since $$I(t) \cdot e^{\frac{t}{T_1}} = \int \frac{d[I(t) \cdot e^{\frac{t}{T_1}}]}{dt} dt = \int e^{\frac{t}{T_1}} \frac{d[I(t)]}{dt} \cdot dt + \frac{1}{T_1} \cdot \int e^{\frac{t}{T_1}} \cdot I(t) \cdot dt, \quad \text{Equation 15}$$

to prove Equation 14, we only need to prove $$\frac{1}{T_1} \cdot \int e^{\frac{t}{T_1}} \cdot I(t) \cdot dt \gg 0. \qquad \text{Equation 16}$$

Equation 16 is true since $$\frac{1}{T_1}, e^{\frac{t}{T_1}},$$

and I(t) are all >>0.
We rewrite Equation 11 below as:

$$N_1 \approx R_{01} \cdot N_0 \cdot T_1 \cdot I(t). \qquad \text{Equation 17}$$

Similarly, from Equation 6 and Equation 17, we have $$\begin{aligned} N_2 &= C_2 \cdot e^{-\frac{t}{T_2}} + R_{12} \cdot e^{-\frac{t}{T_2}} \cdot \int e^{\frac{t}{T_2}} \cdot I(t) \cdot N_1 \cdot dt \\ &\approx C_2 \cdot e^{-\frac{t}{T_2}} + R_{12} \cdot R_{01} \cdot N_0 \cdot T_1 \cdot \\ &\quad e^{-\frac{t}{T_2}} \cdot \int e^{\frac{t}{T_2}} \cdot [I(t)]^2 \cdot dt \\ &\approx R_{12} \cdot R_{01} \cdot N_0 \cdot T_1 \cdot T_2 \cdot I(t)^2, \end{aligned} \qquad \text{Equation 18}$$

where $C_2$ is a constant.
From Equation 7 and Equation 18, we have $$N_3 = R_{23} \cdot \int I(t) \cdot N_2 \cdot dt \approx R_{23} \cdot R_{12} \cdot R_{01} \cdot N_0 \cdot T_1 \cdot T_2 \int I(t)^3 \cdot dt. \qquad \text{Equation 19}$$

At $t \in (\tau, T_L)$, I(t)=0, though there is no input photons, State 3 is populated. Emission will occur following the equation below:

$$\frac{d}{dt} N_3 = -\frac{N_3}{T_3}. \qquad \text{Equation 20}$$

Therefore $$N_3 = -\int_\tau^{T_L} \frac{N_3}{T_3} dt = N_3^0 \cdot e^{-\frac{t-\tau}{T_3}}, \qquad \text{Equation 21}$$

where $N_3^0$ is the electron population density of State 3 at time $\tau$, which is $$N_3^0 = R_{23} \cdot R_{12} \cdot R_{01} \cdot N_0 \cdot T_1 \cdot T_2 \cdot \int I(t)^3 dt = R_{23} \cdot R_{12} \cdot R_{01} \cdot N_0 \cdot T_1 \cdot T_2 \cdot \langle I(t)^3 \rangle \cdot T_L. \qquad \text{Equation 22}$$

Therefore, the detected fluorescence signal is $$\begin{aligned} F \propto \langle N_3(t) \rangle &= \frac{1}{T_L} \cdot \int_0^{T_L} N_3 \, dt = \frac{1}{T_L} \cdot \int_0^{T_L} N_3^0 \cdot \\ &\quad e^{-\frac{t-\tau}{T_3}} dt = \frac{N_3^0}{T_L} \cdot T_3 \cdot \left(1 - e^{-\frac{T_L - \tau}{T_3}}\right) \\ &\approx \frac{N_3^0}{T_L} \cdot T_3. \end{aligned} \qquad \text{Equation 23}$$

By combining Equation 22 and Equation 23, we have $$F \propto \langle N_3(t) \rangle \approx R_{23} \cdot R_{12} \cdot R_{01} \cdot N_0 \cdot T_1 \cdot T_2 \cdot T_3 \cdot \langle I(t)^3 \rangle, \qquad \text{Equation 24}$$

which means $$F \propto \langle I^3 \rangle. \qquad \text{Equation 25}$$

i) Stepwise excitation

In stepwise excitation, the laser pulse width is much shorter than the lifetime of the intermediate states (usually ~$10^{-9}$ s). Then Equation 8 is changed to $$\tau \ll T_1, T_2, T_3. \qquad \text{Equation 26}$$

At $t \in (0, \tau)$, $I(t) \gg 0$, Equation 1-Equation 3 can be simplified as:

$$\frac{d}{dt} N_1 = R_{01} \cdot I(t) \cdot N_0, \qquad \text{Equation 27}$$

$$\frac{d}{dt} N_2 = R_{12} \cdot I(t) \cdot N_1, \qquad \text{Equation 28}$$

$$\frac{d}{dt} N_3 = R_{23} \cdot I(t) \cdot N_2. \qquad \text{Equation 29}$$

From Equation 27

$$N_1 = R_{01} \cdot N_0 \cdot \int I(t) dt. \qquad \text{Equation 30}$$

From Equation 28 and Equation 30, $$N_2 = R_{12} \cdot I(t) \cdot R_{01} \cdot N_0 \cdot \int I(t) \cdot [\int I(t) dt] \cdot dt = \tfrac{1}{2} \cdot R_{12} \cdot R_{01} \cdot N_0 \cdot [\int I(t) dt]^2. \qquad \text{Equation 31}$$

From Equation 29 and Equation 31, $$\begin{aligned} N_3 &= R_{23} \cdot I(t) \cdot \frac{1}{2} \cdot R_{12} \cdot R_{01} \cdot N_0 \cdot \int I(t) \cdot \left[\int I(t)\, dt\right]^2 \cdot dt \\ &= \frac{1}{6} \cdot R_{23} \cdot R_{12} \cdot R_{01} \cdot N_0 \cdot \left[\int I(t)\, dt\right]^3. \end{aligned} \qquad \text{Equation 32}$$

At $t \in (\tau, T_L)$, I(t)=0, Equation 1-Equation 3 can be simplified as:

$$\frac{d}{dt} N_1 = -\frac{N_1}{T_1}, \qquad \text{Equation 33}$$

$$\frac{d}{dt} N_2 = -\frac{N_2}{T_2}, \qquad \text{Equation 34}$$

$$\frac{d}{dt} N_3 = -\frac{N_3}{T_3}. \qquad \text{Equation 35}$$

From Equation 33, $$N_1 = -\int_\tau^{T_L} \frac{N_1}{T_1} dt = N_1^0 \cdot e^{-\frac{t-\tau}{T_1}}, \qquad \text{Equation 36}$$

where $N_1^0$ is the electron population density of State 1 at time $\tau$, which is $$N_0^1 = R_{01} \cdot N_0 \int_0^\tau I(t) dt = R_{01} \cdot N_0 \cdot \langle I(t) \rangle \cdot T_L. \qquad \text{Equation 37}$$

Similarly, from Equation 34 and Equation 37, $$N_2 = N_2^0 \cdot e^{-\frac{t-\tau}{T_2}}, \qquad \text{Equation 38}$$

where $$N_2^0 = 1/2 \cdot R_{12} \cdot R_{01} \cdot N_0 \cdot [\int_0^\tau I(t)dt]^2 = 1/2 \; R_{12} \cdot R_{01} \cdot N_0 \cdot \langle I(t) \rangle^2 \cdot T_L^2.$$

Equation 39

From Equation 35 and Equation 39, $$N_3 = N_3^0 \cdot e^{-\frac{t-\tau}{T_3}},$$

Equation 40 where $$N_3^0 = 1/6 \cdot R_{23} \cdot R_{12} \cdot N_0 \cdot [\int_0^\tau I(t)dt]^3 = 1/6 \; R_{23} \cdot R_{12} \cdot N_0 \cdot \langle I(t) \rangle^3 \cdot T_L^3.$$

Equation 41

Therefore, the detected fluorescence signal $$F \propto \langle N_3(t) \rangle = \frac{1}{T_L} \cdot \int_0^{T_L} N_3 \, dt = \frac{1}{T_L} \cdot \int_0^{T_L} N_3^0 \cdot e^{-\frac{t-\tau}{T_3}} dt = \frac{N_3^0}{T_L} \cdot T_3 \cdot \left(1 - e^{-\frac{T_L - \tau}{T_3}}\right)$$
$$\approx \frac{N_3^0}{T_L} \cdot T_3 \cdot \left(1 - e^{-\frac{T_L}{T_3}}\right)$$
$$= \frac{1}{6} \cdot R_{23} \cdot R_{12} \cdot R_{01} \cdot N_0 \cdot \langle I(t) \rangle^3 \cdot T_L^2 \cdot T_3 \cdot \left(1 - e^{-\frac{T_L}{T_3}}\right),$$

Equation 42 which means $$F \propto N_3 \propto \langle I \rangle^3.$$

Equation 43 a) CW Laser

Assuming that the system has reached equilibrium under the exposure of CW laser with intensity I, we have $$\frac{d}{dt}N_1 = \frac{d}{dt}N_2 = \frac{d}{dt}N_3 = 0.$$

Equation 44

Therefore, Equation 5-Equation 7 can be simplified as:

$$N_1 = R_{01} \cdot I \cdot N_0 \cdot T_1,$$

Equation 45

$$N_2 = R_{12} \cdot I \cdot N_1 \cdot T_2 = R_{12} \cdot R_{01} \cdot I^2 \cdot N_0 \cdot T_2 \cdot T_1,$$

Equation 46

$$N_3 = R_{23} \cdot I \cdot N_2 \cdot T_3 = R_{23} \cdot R_{12} \cdot R_{01} \cdot I^3 \cdot N_0 \cdot T_3 \cdot T_2 \cdot T_1,$$

Equation 47 which means $$F \propto N_3 \propto I^3.$$

Equation 48

Equation 47 is also consistent with Equation 24.

b) Conclusion

Although Equation 25 and Equation 43 appear similar to each other, the difference is significant under a femtosecond pulsed laser. Take the Tsunami laser as an example, with pulsed width $\sim 10^{-13}$ s and period 12.5 ns, $$\frac{\langle I^3 \rangle}{\langle I \rangle^3} \sim 10^{10}.$$

Equation 49

Therefore, stepwise excitation can be readily achieved using a CW laser, whereas simultaneous excitation requires a pulsed laser.

Intermediate States of Melanin SMPAF

Use Equation 47 divided by Equation 42, we have $$\frac{N_3^{CW}}{\langle N_3^{pulsed} \rangle} =$$

$$\frac{R_{23} \cdot R_{12} \cdot R_{01} \cdot I^3 \cdot N_0 \cdot T_3 \cdot T_2 \cdot T_1}{\frac{1}{6} \cdot R_{23} \cdot R_{12} \cdot R_{01} \cdot N_0 \cdot \langle I(t) \rangle^3 \cdot T_L^2 \cdot T_3 \cdot \left(1 - e^{-\frac{T_L}{T_3}}\right)} =$$

$$\frac{6 \cdot T_2 \cdot T_1}{\left(1 - e^{-\frac{T_L}{T_3}}\right) \cdot T_L^2}.$$

Equation 50 the signal strength of melanin SMPAF signal is the same order when using CW or pulsed mode of the Tsunami laser. (J. Kerimo, M. Rajadhyaksha and C. A. DiMarzio, "Enhanced Melanin Fluorescence by Stepwise Three-photon Excitation," *Photochemistry and Photobiology* 87(5), 1042-1049 (2011)) For the Tsunami laser, $T_L \sim 10^{-8}$ s, suppose $T_1 \approx T_2$, then we have $$T_1 \approx T_2 \sim 10^{-9} s.$$

Equation 51 which is consistent with our previous estimate.

To further understand the lifetime of the intermediate states of melanin SMPAF, an optical delay was designed as shown in FIG. 18(a). The laser beam coming from the pulsed laser is separated into two braches by a beam splitter, BS1. The longer path created a delay of $\Delta t$ between the two paths. A tunable neutral density filter is able to control the intensity of the longer path. The longer and shorter paths are then merged by a second beam splitter, BS2, to create a new beam.

Figure 18:
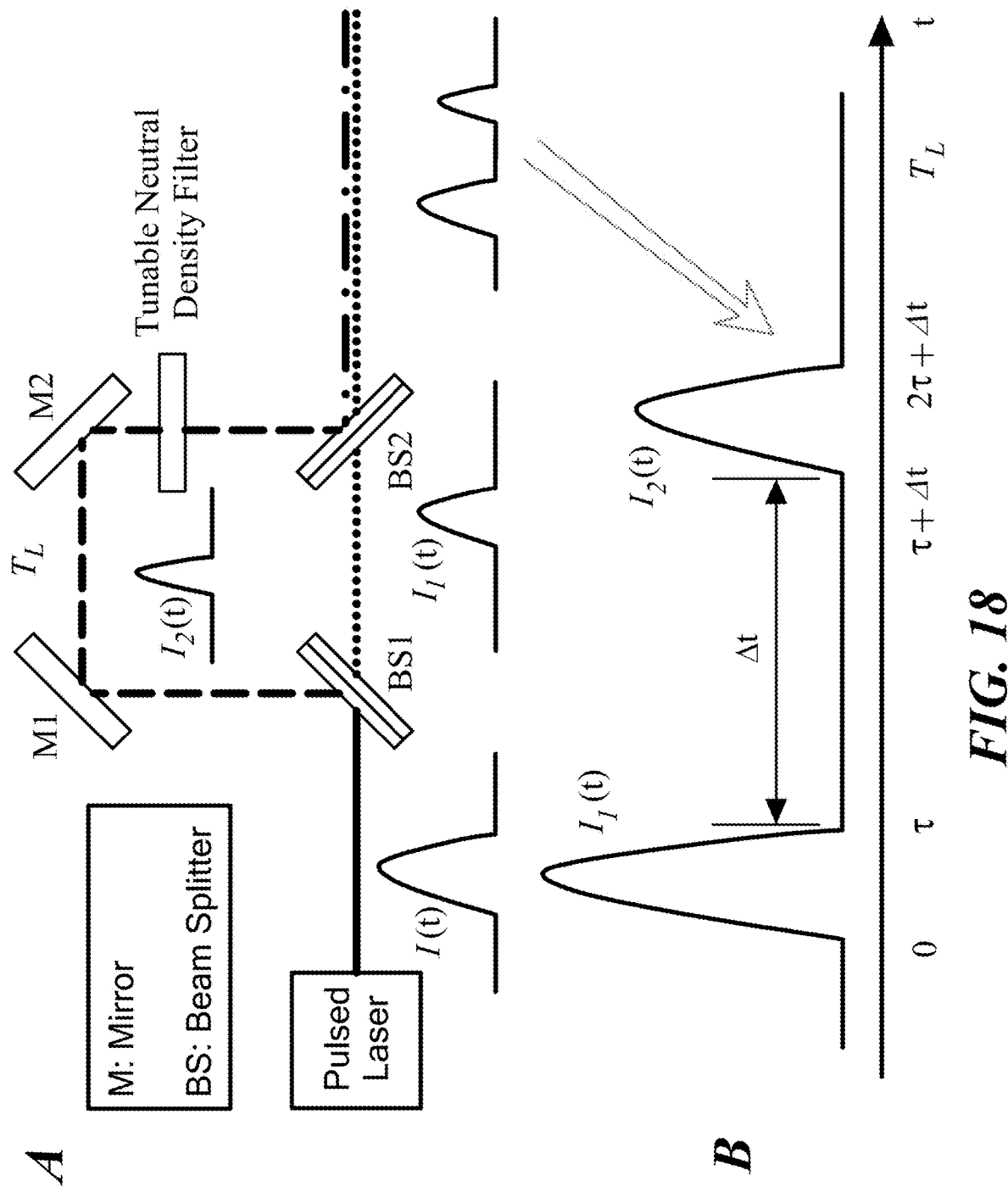
FIG. 18 is a schematic illustration of (a) an experimental setup of an optical configuration to provide an optical delay, and (b) a profile of the output laser beam.

The profile of the new beam is shown in FIG. 18 part B. Two pulses are created at each period $T_L$.

At $t \in (0, \tau)$, $I(t) = I_1(t \gg 0$, from Equation 30-Equation 32, $$N_1 = R_{01} \cdot N_0 \cdot \int I_1(t) dt,$$

Equation 52

$$N_2 = 1/2 \cdot R_{12} \cdot R_{01} \cdot N_0 \cdot [\int I_1(t) dt]^2,$$

Equation 53

$$N_3 = 1/6 \cdot R_{23} \cdot R_{12} \cdot R_{01} \cdot N_0 [\int I_1(t) dt]^3.$$

Equation 54

At $t \in (\tau, \tau + \Delta t)$, $I(t) = 0$, from Equation 36-Equation 41

$$N_1 = N_1^0 \cdot e^{-\frac{t-\tau}{T_1}},$$

Equation 55 where $$N_1^0 = R_{01} \cdot N_0 \int_0^\tau I_1(t) dt;$$

Equation 56

$$N_2 = N_2^0 \cdot e^{-\frac{t-\tau}{T_2}},$$

Equation 57 where $$N_2 = 1/2 \cdot R_{12} \cdot R_{01} \cdot N_0 \cdot [\int_0^\tau I_1(t) dt]^2,$$

Equation 58

$$N_3 = N_3^0 \cdot e^{-\frac{t-\tau}{T_3}},$$

Equation 59 where $$N_3^0 = 1/6 \cdot R_{23} \cdot R_{12} \cdot R_{01} \cdot N_0 [\int_0^\tau I_1(t) dt]^3.$$

Equation 60

When t∈(τ+Δt, 2τ+Δt), I(t)=$I_2$(t). Use $$t' = t - (\tau + \Delta t).$$ Equation 61

Then t'∈(0,τ). From Equation 5, we have:

$$N_1 = C_1 \cdot e^{-\frac{t'}{T_1}} + R_{01} \cdot N_0 \cdot e^{-\frac{t'}{T_1}} \cdot \int e^{\frac{t'}{T_1}} \cdot I_2(t') \cdot dt',$$ Equation 62 where $C_1$ is a constant.

For t'=0, which is t=τ+Δt, from Equation 55, Equation 56 and Equation 62, we have $$N_1(t'=0) =$$ Equation 63

$$N_1^{01} = N_1^0 \cdot e^{-\frac{\Delta t}{T_1}} = e^{-\frac{\Delta t}{T_1}} \cdot R_{01} \cdot N_0 \int_0^\tau I_1(t) dt = C_1.$$

Therefore $$N_1 = R_{01} \cdot N_0 \int_0^\tau I_1(t) dt \cdot e^{-\frac{\Delta t + t'}{T_1}} +$$ Equation 64

$$R_{01} \cdot N_0 \cdot e^{-\frac{t'}{T_1}} \cdot \int e^{\frac{t'}{T_1}} \cdot I_2(t') \cdot dt'.$$

Since t'<τ<<$T_1$, we have $$N_1 \approx R_{01} \cdot N_0 \cdot e^{-\frac{\Delta t}{T_1}} \int_0^\tau I_1(t) dt + R_{01} \cdot N_0 \cdot \int I_2(t') \cdot dt'.$$ Equation 65

Similarly, From Equation 6, we have:

$$N_2 = C_2 \cdot e^{-\frac{t'}{T_2}} + R_{12} \cdot e^{-\frac{t'}{T_2}} \cdot \int e^{\frac{t'}{T_2}} \cdot I_2(t') \cdot N_1 \cdot dt'.$$ Equation 66

For t'=0, from Equation 57, Equation 58 and Equation 66, $$N_2(t'=0) = N_2^{01} = N_2^0 \cdot e^{-\frac{\Delta t}{T_2}} =$$ Equation 67

$$e^{-\frac{\Delta t}{T_2}} \cdot N_2^0 = \frac{1}{2} \cdot R_{12} \cdot R_{01} \cdot N_0 \cdot \left[\int_0^\tau I_1(t) dt\right]^2 = C_2.$$

Therefore, from Equation 65, Equation 66 and Equation 67

$$N_2 = \frac{1}{2} \cdot R_{12} \cdot R_{01} \cdot N_0 \cdot \left[\int_0^\tau I_1(t) dt\right]^2 \cdot e^{-\frac{\Delta t + t'}{T_2}} + R_{12} \cdot e^{-\frac{t'}{T_2}} \cdot$$ Equation 68

$$\int e^{\frac{t'}{T_2}} \cdot I_2(t') \cdot \left[R_{01} \cdot N_0 \cdot e^{-\frac{\Delta t}{T_1}} \int_0^\tau I_1(t) dt + R_{01} \cdot N_0 \cdot \int I_2(t') dt'\right] \cdot dt' =$$

$$\frac{1}{2} \cdot R_{12} \cdot R_{01} \cdot N_0 \cdot \left[\int_0^\tau I_1(t) dt\right]^2 \cdot e^{-\frac{\Delta t + t'}{T_2}} + R_{12} \cdot$$

$$R_{01} \cdot N_0 \cdot e^{-\frac{t'}{T_2}} \cdot \int e^{\frac{t'}{T_2}} \cdot e^{-\frac{\Delta t}{T_1}} \cdot \left[\int_0^\tau I_1(t) dt\right] \cdot I_2(t') \cdot dt' +$$

-continued $$R_{12} \cdot R_{01} \cdot N_0 \cdot e^{-\frac{t'}{T_2}} \cdot \int e^{\frac{t'}{T_2}} \cdot \left[\int I_2(t') dt'\right] \cdot I_2(t') \cdot dt'.$$

Since t'<τ<<$T_1$, $T_2$, we have $$N_2 \approx \frac{1}{2} \cdot R_{12} \cdot R_{01} \cdot N_0 \cdot \left[\int_0^\tau I_1(t) dt\right]^2 \cdot e^{-\frac{\Delta t}{T_2}} +$$ Equation 69

$$R_{12} \cdot R_{01} \cdot N_0 \cdot e^{-\frac{\Delta t}{T_1}} \cdot \left[\int_0^\tau I_1(t) dt\right] \cdot \int I_2(t') \cdot dt' +$$

$$R_{12} \cdot R_{01} \cdot N_0 \cdot \int \left[\int I_2(t') dt'\right] \cdot I_2(t') \cdot dt' =$$

$$\frac{1}{2} \cdot R_{12} \cdot R_{01} \cdot N_0 \cdot \left[\int_0^\tau I_1(t) dt\right]^2 \cdot e^{-\frac{\Delta t}{T_2}} +$$

$$R_{12} \cdot R_{01} \cdot N_0 \cdot e^{-\frac{\Delta t}{T_1}} \cdot \left[\int_0^\tau I_1(t) dt\right] \cdot \int I_2(t') \cdot dt' +$$

$$\frac{1}{2} \cdot R_{12} \cdot R_{01} \cdot N_0 \cdot \left[\int I_2(t') dt'\right]^2.$$

From Equation 7, we have:

$$N_3 = C_3 \cdot e^{-\frac{t'}{T_3}} + R_{23} \cdot e^{-\frac{t'}{T_3}} \cdot \int e^{\frac{t'}{T_3}} \cdot I_2(t') \cdot N_2 \cdot dt'.$$ Equation 70

For t'=0, from Equation 59, Equation 60 and Equation 70, we have $$N_3(t'=0) = N_3^{01} = N_3^0 \cdot e^{-\frac{\Delta t}{T_3}} =$$ Equation 71

$$e^{-\frac{\Delta t}{T_3}} \cdot \frac{1}{6} \cdot R_{23} \cdot R_{12} \cdot R_{01} \cdot N_0 \cdot \left[\int_0^\tau I_1(t) dt\right]^3 = C_3.$$

Therefore, $$N_3 = e^{-\frac{\Delta t}{T_3}} \cdot \frac{1}{6} \cdot R_{23} \cdot R_{12} \cdot R_{01} \cdot N_0 \cdot \left[\int_0^\tau I_1(t) dt\right]^3 \cdot e^{-\frac{t'}{T_3}} +$$ Equation 72

$$R_{23} \cdot e^{-\frac{t'}{T_3}} \cdot \int e^{\frac{t'}{T_3}} \cdot I_2(t') \cdot \left\{\frac{1}{2} \cdot R_{12} \cdot R_{01} \cdot N_0 \cdot \left[\int_0^\tau I_1(t) dt\right]^2 \cdot e^{-\frac{\Delta t}{T_2}} + \right.$$

$$R_{12} \cdot R_{01} \cdot N_0 \cdot e^{-\frac{\Delta t}{T_1}} \cdot \left[\int_0^\tau I_1(t) dt\right] \cdot \int I_2(t') \cdot dt' +$$

$$\left. \frac{1}{2} \cdot R_{12} \cdot R_{01} \cdot N_0 \cdot \left[\int I_2(t') dt'\right]^2 \right\} \cdot dt' =$$

$$\frac{1}{6} \cdot R_{23} \cdot R_{12} \cdot R_{01} \cdot N_0 \cdot \left[\int_0^\tau I_1(t) dt\right]^3 \cdot e^{-\frac{\Delta t}{T_3}} \cdot e^{-\frac{t'}{T_3}} +$$

$$\frac{1}{2} \cdot R_{23} \cdot R_{12} \cdot R_{01} \cdot N_0 \cdot \left[\int_0^\tau I_1(t) dt\right]^2 \cdot e^{-\frac{\Delta t}{T_2}} \cdot e^{-\frac{t'}{T_3}} \cdot \int e^{\frac{t'}{T_3}} \cdot I_2(t') \cdot dt' +$$

$$R_{23} \cdot R_{12} \cdot R_{01} \cdot N_0 \cdot$$

$$\int_0^\tau I_1(t) dt \cdot e^{-\frac{\Delta t}{T_1}} \cdot e^{-\frac{t'}{T_3}} \cdot \int e^{\frac{t'}{T_3}} \cdot I_2(t') \cdot \int I_2(t') dt' \cdot dt' +$$

-continued $$\frac{1}{2} \cdot R_{23} \cdot R_{12} \cdot R_{01} \cdot N_0 \cdot e^{-\frac{t'}{T_3}} \cdot \int e^{\frac{t'}{T_3}} \cdot I_2(t') \cdot \left[\int I_2(t')dt'\right]^2 \cdot dt'.$$

Since $t' < \tau \ll T_1, T_2$, we have

Equation 73

$$N_3 \approx \frac{1}{6} \cdot R_{23} \cdot R_{12} \cdot R_{01} \cdot N_0 \cdot \left[\int_0^\tau I_1(t)dt\right]^3 \cdot e^{-\frac{\Delta t}{T_3}} +$$

$$\frac{1}{2} \cdot R_{23} \cdot R_{12} \cdot R_{01} \cdot N_0 \cdot \left[\int_0^\tau I_1(t)dt\right]^2 \cdot e^{-\frac{\Delta t}{T_2}} \cdot \int I_2(t') \cdot dt' +$$

$$R_{23} \cdot R_{12} \cdot R_{01} \cdot N_0 \cdot \int_0^\tau I_1(t)dt \cdot e^{-\frac{\Delta t}{T_1}} \cdot \int I_2(t') \cdot \int I_2(t')dt' \cdot dt' +$$

$$\frac{1}{2} \cdot R_{23} \cdot R_{12} \cdot R_{01} \cdot N_0 \cdot \int I_2(t') \cdot \left[\int I_2(t')dt'\right]^2 \right\} \cdot dt' =$$

$$\frac{1}{6} \cdot R_{23} \cdot R_{12} \cdot R_{01} \cdot N_0 \cdot \left[\int_0^\tau I_1(t)dt\right]^3 \cdot e^{-\frac{\Delta t}{T_3}} +$$

$$\frac{1}{2} \cdot R_{23} \cdot R_{12} \cdot R_{01} \cdot N_0 \cdot \left[\int_0^\tau I_1(t)dt\right]^2 \cdot e^{-\frac{\Delta t}{T_2}} \cdot \int I_2(t') \cdot dt' +$$

$$\frac{1}{2} \cdot R_{23} \cdot R_{12} \cdot R_{01} \cdot N_0 \cdot \int_0^\tau I_1(t)dt \cdot e^{-\frac{\Delta t}{T_1}} \cdot \left[\int I_2(t')dt'\right]^2 +$$

$$\frac{1}{6} \cdot R_{23} \cdot R_{12} \cdot R_{01} \cdot N_0 \cdot \left[\int I_2(t')dt'\right]^3.$$

When $t \in (2\tau + \Delta t, T_L)$, $I(t) = 0$. From Equation 7

Equation 74

$$N_3 = N_3^{02} \cdot e^{-\frac{t'-\tau}{T_3}},$$

where

Equation 75

$$N_3^{02} = \frac{1}{6} \cdot R_{23} \cdot R_{12} \cdot R_{01} \cdot N_0 \cdot \left[\int_0^\tau I_1(t)dt\right]^3 \cdot e^{-\frac{\Delta t}{T_3}} +$$

$$\frac{1}{2} \cdot R_{23} \cdot R_{12} \cdot R_{01} \cdot N_0 \cdot \left[\int_0^\tau I_1(t)dt\right]^2 \cdot e^{-\frac{\Delta t}{T_2}} \cdot \int_0^\tau I_2(t') \cdot dt' +$$

$$\frac{1}{2} \cdot R_{23} \cdot R_{12} \cdot R_{01} \cdot N_0 \cdot \int_0^\tau I_1(t)dt \cdot e^{-\frac{\Delta t}{T_1}} \cdot \left[\int_0^\tau I_2(t')dt'\right]^2 +$$

$$\frac{1}{6} \cdot R_{23} \cdot R_{12} \cdot R_{01} \cdot N_0 \cdot \left[\int_0^\tau I_2(t')dt'\right]^3.$$

Therefore, the detected fluorescence signal

Equation 76

$$F \propto \langle N_3(t) \rangle =$$

$$\frac{1}{T_L} \cdot \int_0^{T_L} N_3 dt = \frac{1}{T_L} \cdot \left(\int_\tau^{\Delta t + \tau} N_3^0 \cdot e^{-\frac{t-\tau}{T_3}} dt + \int_\tau^{T_L - \Delta t - \tau} N_3^{02} \cdot e^{-\frac{t-\tau}{T_3}} dt\right) =$$

$$\frac{T_3}{T_L} \cdot \left[N_3^0 \cdot \left(1 - e^{-\frac{\Delta t}{T_3}}\right) + N_3^{02} \cdot \left(1 - e^{-\frac{T_L - \Delta t - 2\tau}{T_3}}\right)\right].$$

Therefore, the detected fluorescence signal

Equation 77

$$F \propto \langle N_3(t) \rangle =$$

$$\frac{1}{T_L} \cdot \int_0^{T_L} N_3 dt = \frac{1}{T_L} \cdot \left(\int_\tau^{\Delta t + \tau} N_3^0 \cdot e^{-\frac{t-\tau}{T_3}} dt + \int_\tau^{T_L - \Delta t - \tau} N_3^{02} \cdot e^{-\frac{t-\tau}{T_3}} dt\right) =$$

$$\frac{T_3}{T_L} \cdot \left[N_3^0 \cdot \left(1 - e^{-\frac{\Delta t}{T_3}}\right) + N_3^{02} \cdot \left(1 - e^{-\frac{T_L - \Delta t - 2\tau}{T_3}}\right)\right].$$

Again $t' < \tau \ll T_1, T_2$, then

Equation 78

$$\langle N_3(t) \rangle \approx \frac{T_3}{T_L} \cdot \left[N_3^0 - N_3^0 \cdot e^{-\frac{\Delta t}{T_3}} + N_3^{02} - N_3^{02} \cdot e^{-\frac{T_L - \Delta t}{T_3}}\right].$$

From Equation 60 and Equation 75,

Equation 79

$$\langle N_3(t) \rangle \approx \frac{T_3}{T_L} \cdot \left\{\frac{1}{6} \cdot R_{23} \cdot R_{12} \cdot R_{01} \cdot N_0 \cdot \left[\int_0^\tau I_1(t)dt\right]^3 - \right.$$

$$\frac{1}{6} \cdot R_{23} \cdot R_{12} \cdot R_{01} \cdot N_0 \cdot \left[\int_0^\tau I_1(t)dt\right]^3 \cdot e^{-\frac{\Delta t}{T_3}} +$$

$$\frac{1}{6} \cdot R_{23} \cdot R_{12} \cdot R_{01} \cdot N_0 \cdot \left[\int_0^\tau I_1(t)dt\right]^3 \cdot e^{-\frac{\Delta t}{T_3}} +$$

$$\frac{1}{2} \cdot R_{23} \cdot R_{12} \cdot R_{01} \cdot N_0 \cdot \left[\int_0^\tau I_1(t)dt\right]^2 \cdot e^{-\frac{\Delta t}{T_2}} \cdot \int_0^\tau I_2(t') \cdot dt' +$$

$$\frac{1}{2} \cdot R_{23} \cdot R_{12} \cdot R_{01} \cdot N_0 \cdot \int_0^\tau I_1(t)dt \cdot e^{-\frac{\Delta t}{T_1}} \cdot \left[\int_0^\tau I_1(t')dt'\right]^2 +$$

$$\frac{1}{6} \cdot R_{23} \cdot R_{12} \cdot R_{01} \cdot N_0 \cdot \left[\int_0^\tau I_2(t') \cdot dt'\right]^3 -$$

$$\left\{\frac{1}{6} \cdot R_{23} \cdot R_{12} \cdot R_{01} \cdot N_0 \cdot \left[\int_0^\tau I_1(t)dt\right]^3 \cdot e^{-\frac{\Delta t}{T_3}} + \right.$$

$$\frac{1}{2} \cdot R_{23} \cdot R_{12} \cdot R_{01} \cdot N_0 \cdot \left[\int_0^\tau I_1(t)dt\right]^2 \cdot e^{-\frac{\Delta t}{T_2}} \cdot \int_0^\tau I_2(t') \cdot dt' +$$

$$\frac{1}{2} \cdot R_{23} \cdot R_{12} \cdot R_{01} \cdot N_0 \cdot \int_0^\tau I_1(t)dt \cdot e^{-\frac{\Delta t}{T_1}} \cdot \left[\int_0^\tau I_2(t') \cdot dt'\right]^2 +$$

$$\left. \frac{1}{6} \cdot R_{23} \cdot R_{12} \cdot R_{01} \cdot N_0 \cdot \left[\int_0^\tau I_2(t') \cdot dt'\right]^3 \right\} \cdot e^{-\frac{T_L - \Delta t}{T_3}} \right\} =$$

$$\frac{R_{23} \cdot R_{12} \cdot R_{01} \cdot N_0 \cdot T_3}{T_L} \cdot \left\{\frac{1}{6} \cdot \left[\int_0^\tau I_1(t)dt\right]^3 + \right.$$

$$\frac{1}{2} \cdot \left[\int_0^\tau I_1(t)dt\right]^2 \cdot e^{-\frac{\Delta t}{T_2}} \cdot \int_0^\tau I_2(t') \cdot dt' +$$

$$\frac{1}{2} \cdot \int_0^\tau I_1(t)dt \cdot e^{-\frac{\Delta t}{T_1}} \cdot \left[\int_0^\tau I_2(t') \cdot dt'\right]^2 + \frac{1}{6} \cdot \left[\int_0^\tau I_2(t') \cdot dt'\right]^3 -$$

$$\left\{\frac{1}{6} \cdot \left[\int_0^\tau I_1(t)dt\right]^3 \cdot e^{-\frac{\Delta t}{T_3}} + \frac{1}{2} \cdot \left[\int_0^\tau I_1(t)dt\right]^2 \cdot e^{-\frac{\Delta t}{T_2}} \cdot \int_0^\tau I_2(t') \cdot dt' + \right.$$

$$\frac{1}{2} \cdot \int_0^\tau I_1(t) \cdot dt \cdot e^{-\frac{\Delta t}{T_1}} \cdot \left[\int_0^\tau I_2(t') \cdot dt'\right]^2 +$$

$$\left. \left. \frac{1}{6} \cdot \left[\int_0^\tau I_2(t') \cdot dt'\right]^3 \right\} \cdot e^{-\frac{T_L - \Delta t}{T_3}} \right\}.$$

By definition $$\langle I_1(t)\rangle = \frac{1}{T_L} \cdot \int_0^T I_1(t)dt, \quad \text{Equation 80}$$

$$\langle I_2(t)\rangle = \frac{1}{T_L} \cdot \int_0^T I_2(t')dt'. \quad \text{Equation 81}$$

From Equation 79, Equation 80 and Equation 81, we have

Equation 82

$$\langle N_3(t)\rangle = \frac{1}{6} \cdot R_{23} \cdot R_{12} \cdot R_{01} \cdot N_0 \cdot T_3 \cdot$$

$$T_L^2 \cdot \left[ \langle I_1(t)\rangle^3 \cdot \left(1 - e^{-\frac{T_L}{T_3}}\right) + 3 \cdot \langle I_2(t)\rangle^2 \cdot \langle I_2(t)\rangle \cdot e^{-\frac{\Delta t}{T_2}} \cdot \left(1 - e^{-\frac{T_L - \Delta t}{T_3}}\right) + \right.$$

$$\left. 3 \cdot \langle I_2(t)\rangle \cdot \langle I_2(t)\rangle^2 \cdot e^{-\frac{\Delta t}{T_1}} \cdot \left(1 - e^{-\frac{T_L - \Delta t}{T_3}}\right) + \langle I_2(t)\rangle^3 \cdot \left(1 - e^{-\frac{T_L - \Delta t}{T_3}}\right) \right].$$

Let $T_L \gg T_3$, and $T_L - \Delta t \gg T_3$, then

Equation 83

$$F \propto \langle N_3(t)\rangle \approx \frac{1}{6} \cdot R_{23} \cdot R_{12} \cdot R_{01} \cdot N_0 \cdot T_3 \cdot T_L^2 \cdot$$

$$\left( \langle I_1(t)\rangle^3 + 3 \cdot \langle I_1(t)\rangle^2 \cdot \langle I_2(t)\rangle \cdot e^{-\frac{\Delta t}{T_2}} + 3 \cdot \langle I_1(t)\rangle \cdot \langle I_2(t)\rangle^2 \cdot e^{-\frac{\Delta t}{T_1}} + \langle I_1(t)\rangle^3 \right).$$

If we block the orange path, $I_2(t)=0$, then $$\langle N_3^1\rangle = \frac{1}{6}R_{23}\cdot R_{12}\cdot R_{01}\cdot N_0\cdot T_3\cdot T_L^2 \cdot \langle I_1(t)\rangle^3. \quad \text{Equation 84}$$

Equation 84 is consistent with our previous work (Equation 42 when $T_L \gg T_3$).

Use Equation 83 divide by Equation 84, we have $$\frac{F_3^{1\&2}}{F_3^1} = \quad \text{Equation 85}$$

$$\frac{\langle N_3^{1\&2}\rangle}{\langle N_3^1\rangle} = \frac{\langle I_1(t)\rangle^3 + 3\cdot\langle I_1(t)\rangle^2\cdot\langle I_1(t)\rangle\cdot e^{-\frac{\Delta t}{T_2}} + 3\cdot\langle I_1(t)\rangle\cdot\langle I_1(t)\rangle^2\cdot e^{-\frac{\Delta t}{T_1}} + \langle I_1(t)\rangle^3}{\langle I_1(t)\rangle^3}.$$

Therefore, by varying $I_2(t)$ using the neutral density filter and meanwhile monitoring the fluorescence signal, we can solve $T_1$ and $T_2$, which are the lifetime of the intermediate states.

The method and system can be used for the treatment of melanin-related diseases and conditions in subjects in need thereof. Melanin-related diseases can include, without limitation, melanocytic lesions, congenital or acquired hyperpigmentation/melanin deposition, and other skin discoloration due to deposition, for example, associated with metals (such as mercury poisoning) or as a side effect from drug usage. Melanocytic lesions can include, for example, benign nevi and malignant melanoma. Hyperpigmentation/melanin deposition can include or arise from, for example, melasma; chronic nutritional deficiency; congenital pigment deposition, such as Addison's disease or McCune-Albright syndrome; sun damage, such as solar lentigo or deposition sun damage; ephelides (freckles); café au lait macules; nevus of Ota and Ito; post inflammatory hyperpigmentations; nevus spilus; seborrheic keratoses; blue nevi; and Becker's nevus. The method and system are useful for treatment of melanin-related diseases in sensitive areas, such as in or near the eye, where damage to surrounding tissue is difficult to avoid using traditional techniques. The method and system can also be used for cosmetic applications, such as correction of uneven skin tone, including vitiligo, skin lightening, freckle removal, or hair removal. For hair removal, the method and system can be used to ablate the melanin that is present in the hair shaft, thereby damaging the follicular epithelium. The method and system can be used to treat human and non-human animal subjects.

The present method and system advantageously utilize SMPAF of melanin to guide melanin removal. The method and system can also advantageously utilize a low-cost continuous wave laser for melanin removal, in contrast to the more high-cost pulsed lasers used in photothermolysis techniques. It will be appreciated that a pulsed laser could, however, be used if desired.

The method and system can achieve high precision in the ablation, on the order of 1 μm and smaller. The high power level laser of the method and system is able to target individual melanin particles or grains. The high resolution results in no or minimal collateral damage to other components of the tissue. Use of a near-infrared laser can achieve deeper penetration of the skin compared to other wavelengths used in traditional technologies.

It will be appreciated that the various features of the embodiments described herein can be combined in a variety of ways. For example, a feature described in conjunction with one embodiment may be included in another embodiment even if not explicitly described in conjunction with that embodiment.

The present invention has been described in conjunction with certain preferred embodiments. It is to be understood that the invention is not limited to the exact details of construction, operation, exact materials or embodiments shown and described, and that various modifications, substitutions of equivalents, alterations to the compositions, and other changes to the embodiments disclosed herein will be apparent to one of skill in the art.

What is claimed is:

1. A system for ablating melanin comprising:
   an objective lens assembly disposed on an optical path to focus light on an image plane within a region of tissue including melanin;
   a first light source disposed to transmit a first light beam on the optical path to the image plane within the region of tissue, the first light beam comprising a wavelength sufficient to induce step-wise multi-photon fluorescence of melanin in the image plane;
   a detector disposed to receive a step-wise multi-photon fluorescence signal from the melanin in the image plane returning along at least a portion of the optical path; and
   a second light source disposed to direct a second light beam on the optical path to the image plane within the region of tissue, the second light beam comprising a wavelength and intensity sufficient to ablate melanin in the image plane within the region of tissue.

2. The system of claim 1, further comprising a controller in communication with the objective lens assembly, the first light source, the second light source, and the detector, wherein the controller is operative to store detected fluorescence signals from the melanin in the image plane and to control the second light source to ablate melanin at locations in the tissue corresponding to the detected fluorescence signals.

3. The system of claim 1, further comprising a processor and a memory comprising instructions for carrying out a method comprising the steps of:
inducing stepwise multi-photon fluorescence in melanin within a region of tissue;
detecting the fluorescence from the melanin in the region; and
ablating at least a portion of the melanin from which the fluorescence is detected.

4. The system of claim 1, wherein the first light source is a continuous wave laser and the second light source is a continuous wave laser.

5. The system of claim 1, wherein the second light source is a continuous wave laser or a pulsed laser.

6. The system of claim 1, wherein the wavelength of the first light beam is in the range from 600 nm to 2 μm and the wavelength of the second light beam is in the range from 600 nm to 2 μm.

7. The system of claim 1, wherein the first light source operates at a lower power than the second light source.

8. The system of claim 1, wherein the first light source is separate from the second light source.

9. The system of claim 1, wherein a single light source operable at selectable power levels serves as the first light source and the second light source.

10. The system of claim 1, wherein the second light beam is operable to ablate melanin at a resolution of less than 10 μm in the image plane.

11. The system of claim 1, wherein the second light beam is operable to ablate melanin at a resolution of less than 1 μm in the image plane.

12. The system of claim 1, wherein the second light beam is operable to ablate a single melanin grain.

13. The system of claim 1, wherein the detector is selected from the group consisting of a photon detector, a photomultiplier tube, avalanche photodiodes, a spectrometer, a CCD image array detector, and a CMOS photodiode array detector.

14. The system of claim 1, further comprising a scanning system operative to scan the light beams from the first light source and the second light source across the image plane.

15. The system of claim 14, wherein the scanning system comprises one or two scanning mirrors disposed to scan in orthogonal directions.

16. The system of claim 14, wherein the scanning system comprises a galvanometer mirror scanner and/or a rotating polygonal mirror scanner.

17. The system of claim 14, further comprising a controller in communication with the objective lens assembly, the first light source, the second light source, the scanner, and the detector, wherein the controller is operative to scan the first light source over the region of tissue to induce the stepwise multi-photon fluorescence, to generate a map specifying areas of the detected fluorescence in the region, and to move the second light source to the areas of the detected fluorescence specified in the map.

18. The system of claim 17, wherein the controller is operative to move the first light source to a further region of tissue, store detected fluorescence signals from the melanin in the further region, and control the second light source to ablate at least a portion of the melanin from which the fluorescence is detected in the further region.

19. The system of claim 18, wherein the controller is operative to control repetition of the steps of inducing stepwise multi-photon fluorescence in melanin, detecting the fluorescence from the melanin, and ablating at least a portion of the melanin from which the fluorescence is detected at a new region of tissue.

20. The system of claim 17, wherein the controller is operative to monitor fluorescence from the region after ablation to determine whether ablation has been completed.

21. The system of claim 1, further comprising a movable stage for support of a body part comprising the region of tissue, wherein the stage is movable with respect to the image plane, and wherein the system is configured so that fluorescence of melanin in multiple image planes can be induced and at least a portion of the melanin in multiple image planes can be ablated.

22. The system of claim 1, wherein at least the objective lens assembly and a portion of the optical path from the first light source and the second light source are housed within a hand-held device.

* * * * *